(12) United States Patent
McCullough et al.

(10) Patent No.: US 11,357,916 B2
(45) Date of Patent: Jun. 14, 2022

(54) DRUG DELIVERY DEVICE WITH LIVE BUTTON OR USER INTERFACE FIELD

(71) Applicant: AMGEN INC., Thousand Oaks, CA (US)

(72) Inventors: Adam B. McCullough, Westlake Village, CA (US); Scott R. Gibson, Granada Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/522,387

(22) PCT Filed: Dec. 10, 2015

(86) PCT No.: PCT/US2015/064869
§ 371 (c)(1),
(2) Date: Apr. 27, 2017

(87) PCT Pub. No.: WO2016/100055
PCT Pub. Date: Jun. 23, 2016

(65) Prior Publication Data
US 2017/0368260 A1 Dec. 28, 2017

Related U.S. Application Data

(60) Provisional application No. 62/094,516, filed on Dec. 19, 2014.

(51) Int. Cl.
*A61M 5/20* (2006.01)
*A61M 5/24* (2006.01)
(Continued)

(52) U.S. Cl.
CPC ........ *A61M 5/2459* (2013.01); *A61M 5/1452* (2013.01); *A61M 5/14248* (2013.01);
(Continued)

(58) Field of Classification Search
CPC ................... A61M 2005/208; A61M 2205/13
See application file for complete search history.

(56) References Cited

U.S. PATENT DOCUMENTS 4,386,606 A   6/1983   Tretinyak et al.
4,417,889 A   11/1983  Choi
(Continued)

FOREIGN PATENT DOCUMENTS

EP   2716317 A1    4/2014
JP   2009514572 A  4/2009
(Continued)

OTHER PUBLICATIONS

International Preliminary Report on Patentability and Written Opinion for International Application No. PCT/US2015/064869, dated Jun. 20, 2017.
(Continued)

*Primary Examiner* — William R Carpenter
(74) *Attorney, Agent, or Firm* — Marshall, Gerstein & Borun LLP

(57) ABSTRACT

A drug delivery device includes a container for storing a drug, the container having a stopper for expelling the drug; an injection drive comprising an energy source for directly or indirectly acting on the stopper to expel the drug; a sensor for detecting contact between the drug delivery device and a body of a patient; and a user interface (UI) for activating or causing the activation of the injection drive. The device is operative for drawing attention to the UI, if the sensor detects contact between the drug delivery device and the body of the patient, to thereby indicate that the injection drive is ready to be activated, which activation is the next step in the drug administration process.

16 Claims, 17 Drawing Sheets

(51) Int. Cl.
   *A61M 5/142* (2006.01)
   *A61M 5/32* (2006.01)
   *A61M 5/145* (2006.01)
   *A61M 5/315* (2006.01)
   *A61M 5/28* (2006.01)
   *A61M 5/31* (2006.01)

(52) U.S. Cl.
   CPC ............ *A61M 5/20* (2013.01); *A61M 5/2033* (2013.01); *A61M 5/2053* (2013.01); *A61M 5/3158* (2013.01); *A61M 5/3202* (2013.01); *A61M 5/3243* (2013.01); *A61M 5/1454* (2013.01); *A61M 5/14526* (2013.01); *A61M 5/28* (2013.01); *A61M 2005/206* (2013.01); *A61M 2005/208* (2013.01); *A61M 2005/2462* (2013.01); *A61M 2005/3125* (2013.01); *A61M 2205/13* (2013.01); *A61M 2205/3306* (2013.01); *A61M 2205/3313* (2013.01); *A61M 2205/3317* (2013.01); *A61M 2205/502* (2013.01); *A61M 2205/581* (2013.01); *A61M 2205/582* (2013.01); *A61M 2205/583* (2013.01); *A61M 2205/584* (2013.01); *A61M 2205/587* (2013.01)

(56) References Cited

U.S. PATENT DOCUMENTS

| | | |
|---|---|---|
| 4,559,038 A | 12/1985 | Berg et al. |
| 4,703,008 A | 10/1987 | Lin |
| 5,441,868 A | 8/1995 | Lin |
| 5,505,706 A | 4/1996 | Maus et al. |
| 5,547,933 A | 8/1996 | Lin |
| 5,582,593 A | 12/1996 | Hultman |
| 5,618,698 A | 4/1997 | Lin |
| 5,621,080 A | 4/1997 | Lin |
| 5,686,292 A | 11/1997 | Schwall et al. |
| 5,756,349 A | 5/1998 | Lin |
| 5,767,078 A | 6/1998 | Johnson et al. |
| 5,773,569 A | 6/1998 | Wrighton et al. |
| 5,789,554 A | 8/1998 | Leung et al. |
| 5,830,851 A | 11/1998 | Wrighton et al. |
| 5,856,298 A | 1/1999 | Strickland |
| 5,879,143 A | 3/1999 | Cote et al. |
| 5,955,422 A | 9/1999 | Lin |
| 5,986,047 A | 11/1999 | Wrighton et al. |
| 6,030,086 A | 2/2000 | Thomas |
| 6,063,053 A | 5/2000 | Castellano et al. |
| 6,183,441 B1 | 2/2001 | Kriesel et al. |
| 6,310,078 B1 | 10/2001 | Connolly et al. |
| 6,355,019 B1 | 3/2002 | Kriesel et al. |
| 6,391,633 B1 | 5/2002 | Stern et al. |
| 6,468,529 B1 | 10/2002 | Schwall et al. |
| 6,562,596 B1 | 5/2003 | Silbiger et al. |
| 6,583,272 B1 | 6/2003 | Bailon |
| 6,586,398 B1 | 7/2003 | Kinstler et al. |
| 6,648,821 B2 | 11/2003 | Lebel et al. |
| 6,740,059 B2 * | 5/2004 | Flaherty ............ A61M 5/14248 604/67 |
| 6,750,369 B2 | 6/2004 | Connolly et al. |
| 6,756,480 B2 | 6/2004 | Kostenuik et al. |
| 6,803,453 B1 | 10/2004 | Brunkow et al. |
| 6,835,809 B1 | 12/2004 | Liu et al. |
| 6,878,136 B2 | 4/2005 | Fleury et al. |
| 6,900,292 B2 | 5/2005 | Sun et al. |
| 6,918,894 B2 | 7/2005 | Fleury et al. |
| 6,919,426 B2 | 7/2005 | Boone et al. |
| 6,958,705 B2 | 10/2005 | Lebel et al. |
| 6,974,437 B2 | 12/2005 | Lebel et al. |
| 7,030,226 B2 | 4/2006 | Sun et al. |
| 7,037,498 B2 | 5/2006 | Cohen et al. |
| 7,084,245 B2 | 8/2006 | Holmes et al. |
| 7,153,507 B2 | 12/2006 | van de Winkel et al. |
| 7,217,689 B1 | 5/2007 | Elliott et al. |
| 7,220,245 B2 | 5/2007 | Kriesel |
| 7,220,410 B2 | 5/2007 | Kim et al. |
| 7,223,593 B2 | 5/2007 | Coffin |
| 7,510,544 B2 | 3/2009 | Vilks et al. |
| 7,521,048 B2 | 4/2009 | Gliniak et al. |
| 7,537,924 B2 | 5/2009 | Coffin |
| 7,645,263 B2 | 1/2010 | Angel et al. |
| 7,766,873 B2 | 8/2010 | Moberg et al. |
| 7,831,310 B2 | 11/2010 | Lebel et al. |
| 7,871,399 B2 | 1/2011 | Dacquay et al. |
| 7,875,022 B2 | 1/2011 | Wenger et al. |
| 7,951,122 B2 | 5/2011 | Shekalim |
| 7,967,773 B2 | 6/2011 | Amborn et al. |
| 7,976,493 B2 | 7/2011 | Carter et al. |
| 7,976,500 B2 | 7/2011 | Adams et al. |
| 7,976,505 B2 | 7/2011 | Hines et al. |
| 7,981,669 B2 | 7/2011 | Coffin et al. |
| 8,016,789 B2 | 9/2011 | Grant et al. |
| 8,128,597 B2 | 3/2012 | Cross et al. |
| 8,147,451 B2 | 4/2012 | Brockman et al. |
| 8,231,577 B2 | 7/2012 | Carter et al. |
| 8,303,535 B2 | 11/2012 | Both et al. |
| 8,361,030 B2 | 1/2013 | Carter |
| 8,414,523 B2 | 4/2013 | Blomquist et al. |
| 8,439,879 B2 | 5/2013 | Shekalim |
| 8,454,557 B1 | 6/2013 | Qi et al. |
| 8,529,500 B2 | 9/2013 | Bingham et al. |
| 8,647,302 B2 | 2/2014 | Briones et al. |
| 8,717,141 B2 | 5/2014 | Eberhart et al. |
| 8,784,380 B2 | 7/2014 | Wall |
| 8,821,454 B2 | 9/2014 | Kriesel et al. |
| 8,905,974 B2 | 12/2014 | Carter et al. |
| 8,998,842 B2 | 4/2015 | Lauchard et al. |
| 9,008,764 B2 | 4/2015 | Larsen |
| 9,114,208 B2 | 8/2015 | Smith et al. |
| 9,132,231 B2 | 9/2015 | Gross et al. |
| 9,211,378 B2 | 12/2015 | Boit et al. |
| 2001/0027294 A1 | 10/2001 | Kriesell et al. |
| 2001/0039397 A1 | 11/2001 | Kriesell et al. |
| 2002/0155998 A1 | 10/2002 | Young et al. |
| 2003/0023586 A1 | 1/2003 | Knorr |
| 2003/0077753 A1 | 4/2003 | Tischer |
| 2003/0082749 A1 | 5/2003 | Sun et al. |
| 2003/0138421 A1 | 7/2003 | van de Winkel et al. |
| 2003/0143202 A1 | 7/2003 | Binley et al. |
| 2003/0195156 A1 | 10/2003 | Min et al. |
| 2003/0229023 A1 | 12/2003 | Oliner et al. |
| 2003/0235582 A1 | 12/2003 | Singh et al. |
| 2004/0009902 A1 | 1/2004 | Boime et al. |
| 2004/0018191 A1 | 1/2004 | Wang et al. |
| 2004/0035491 A1 | 2/2004 | Castellano |
| 2004/0071694 A1 | 4/2004 | DeVries et al. |
| 2004/0071702 A1 | 4/2004 | van de Winkel et al. |
| 2004/0086503 A1 | 5/2004 | Cohen et al. |
| 2004/0091961 A1 | 5/2004 | Evans et al. |
| 2004/0097712 A1 | 5/2004 | Varnum et al. |
| 2004/0143857 A1 | 7/2004 | Young et al. |
| 2004/0157293 A1 | 8/2004 | Evans et al. |
| 2004/0175379 A1 | 9/2004 | DeVries et al. |
| 2004/0175824 A1 | 9/2004 | Sun et al. |
| 2004/0181033 A1 | 9/2004 | Han et al. |
| 2004/0202655 A1 | 10/2004 | Morton et al. |
| 2004/0228859 A1 | 11/2004 | Graus et al. |
| 2004/0229318 A1 | 11/2004 | Heavner |
| 2004/0248815 A1 | 12/2004 | Connolly et al. |
| 2004/0265307 A1 | 12/2004 | Singh et al. |
| 2004/0266690 A1 | 12/2004 | Pool |
| 2005/0008642 A1 | 1/2005 | Graus et al. |
| 2005/0019914 A1 | 1/2005 | Staerk et al. |
| 2005/0020980 A1 | 1/2005 | Inoue et al. |
| 2005/0026834 A1 | 2/2005 | Cox et al. |
| 2005/0027264 A1 | 2/2005 | Fleury et al. |
| 2005/0065472 A1 | 3/2005 | Cindrich et al. |
| 2005/0074821 A1 | 4/2005 | Wild et al. |
| 2005/0084906 A1 | 4/2005 | Goetsch et al. |
| 2005/0096461 A1 | 5/2005 | Cox |
| 2005/0107297 A1 | 5/2005 | Holmes et al. |
| 2005/0107591 A1 | 5/2005 | Cox |
| 2005/0112694 A1 | 5/2005 | Carter et al. |

(56) References Cited

U.S. PATENT DOCUMENTS

| | | |
|---|---|---|
| 2005/0118643 A1 | 6/2005 | Burgess et al. |
| 2005/0124045 A1 | 6/2005 | Sun et al. |
| 2005/0124564 A1 | 6/2005 | Binley et al. |
| 2005/0136063 A1 | 6/2005 | Wang et al. |
| 2005/0137329 A1 | 6/2005 | Holmes et al. |
| 2005/0142642 A1 | 6/2005 | Sun et al. |
| 2005/0143292 A1 | 6/2005 | DeFrees et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0170457 A1 | 8/2005 | Pool et al. |
| 2005/0181359 A1 | 8/2005 | Optelten et al. |
| 2005/0181482 A1 | 8/2005 | Meade et al. |
| 2005/0186203 A1 | 8/2005 | Singh et al. |
| 2005/0192211 A1 | 9/2005 | Gillies et al. |
| 2005/0202538 A1 | 9/2005 | Gillies et al. |
| 2005/0227289 A1 | 10/2005 | Reilly et al. |
| 2005/0244408 A1 | 11/2005 | Cohen et al. |
| 2005/0244409 A1 | 11/2005 | Erickson-Miller et al. |
| 2005/0249728 A1 | 11/2005 | Singh et al. |
| 2006/0040358 A1 | 2/2006 | Ligensa et al. |
| 2006/0088906 A1 | 4/2006 | DeFrees et al. |
| 2006/0111279 A1 | 5/2006 | DeFrees et al. |
| 2006/0135431 A1 | 6/2006 | Min et al. |
| 2007/0038181 A1 | 2/2007 | Melamud et al. |
| 2007/0066939 A1 | 3/2007 | Krulevitch et al. |
| 2007/0100288 A1 | 5/2007 | Bozeman et al. |
| 2007/0110747 A1 | 5/2007 | Paszty et al. |
| 2007/0219480 A1* | 9/2007 | Kamen ............ F04B 43/02 604/20 |
| 2007/0250019 A1 | 10/2007 | Fleury et al. |
| 2007/0253951 A1 | 11/2007 | Ng et al. |
| 2008/0091139 A1 | 4/2008 | Srinivasan et al. |
| 2008/0132844 A1 | 6/2008 | Peterson et al. |
| 2008/0166352 A1 | 7/2008 | Siu et al. |
| 2008/0195056 A1* | 8/2008 | Bishop ............ A61M 5/42 604/218 |
| 2008/0221523 A1 | 9/2008 | Moberg et al. |
| 2008/0234625 A1 | 9/2008 | Dacquay et al. |
| 2008/0262427 A1* | 10/2008 | Hommann ........ A61M 5/2033 604/131 |
| 2008/0281273 A1 | 11/2008 | Angel et al. |
| 2009/0043290 A1 | 2/2009 | Villegas et al. |
| 2009/0082730 A1 | 3/2009 | Nguyen et al. |
| 2009/0088690 A1 | 4/2009 | Carter et al. |
| 2009/0099525 A1 | 4/2009 | Lawson |
| 2009/0156989 A1 | 6/2009 | Carter et al. |
| 2009/0177142 A1 | 7/2009 | Blomquist et al. |
| 2009/0182277 A1 | 7/2009 | Carter |
| 2009/0192471 A1 | 7/2009 | Carter et al. |
| 2009/0234106 A1 | 9/2009 | Han et al. |
| 2009/0240240 A1 | 9/2009 | Hines et al. |
| 2009/0326472 A1 | 12/2009 | Carter et al. |
| 2010/0010418 A1* | 1/2010 | Nisato ............ A61K 47/32 604/20 |
| 2010/0094222 A1 | 4/2010 | Grant et al. |
| 2010/0121274 A1 | 5/2010 | Oh et al. |
| 2010/0137801 A1 | 6/2010 | Streit et al. |
| 2010/0152658 A1 | 6/2010 | Hanson et al. |
| 2010/0152666 A1 | 6/2010 | Carter et al. |
| 2010/0166768 A1 | 7/2010 | Sleeman et al. |
| 2010/0198182 A1 | 8/2010 | Lanigan et al. |
| 2010/0198183 A1 | 8/2010 | Lanigan et al. |
| 2010/0253476 A1 | 10/2010 | Poutiatine et al. |
| 2010/0286467 A1 | 11/2010 | Pesach et al. |
| 2011/0022002 A1 | 1/2011 | Hanson et al. |
| 2011/0066012 A1 | 3/2011 | Hanson et al. |
| 2011/0077614 A1 | 3/2011 | Shay |
| 2011/0112484 A1 | 5/2011 | Carter et al. |
| 2011/0118672 A1 | 5/2011 | Hanson et al. |
| 2011/0160696 A1 | 6/2011 | Hoss |
| 2011/0166512 A1* | 7/2011 | Both ............ A61M 5/14248 604/67 |
| 2011/0205065 A1 | 8/2011 | Strachan et al. |
| 2011/0218489 A1 | 9/2011 | Mastrototaro et al. |
| 2011/0224601 A1 | 9/2011 | Shekalim |
| 2011/0230838 A1 | 9/2011 | Adams et al. |
| 2012/0010594 A1* | 1/2012 | Holt ............ A61M 5/14248 604/506 |
| 2012/0022499 A1 | 1/2012 | Anderson et al. |
| 2012/0025995 A1 | 2/2012 | Moberg et al. |
| 2012/0029385 A1 | 2/2012 | Chong et al. |
| 2012/0041370 A1 | 2/2012 | Moberg et al. |
| 2012/0041415 A1 | 2/2012 | Estes et al. |
| 2012/0078170 A1 | 3/2012 | Smith et al. |
| 2012/0078181 A1* | 3/2012 | Smith ............ A61M 5/16804 604/152 |
| 2012/0078182 A1 | 3/2012 | Smith et al. |
| 2012/0078184 A1 | 3/2012 | Smith et al. |
| 2012/0078185 A1 | 3/2012 | Smith et al. |
| 2012/0078217 A1 | 3/2012 | Smith et al. |
| 2012/0116309 A1 | 5/2012 | Bazargan et al. |
| 2012/0209194 A1 | 8/2012 | Lanigan et al. |
| 2012/0209196 A1 | 8/2012 | Lanigan et al. |
| 2012/0310169 A1 | 12/2012 | Sonderegger et al. |
| 2012/0310173 A1 | 12/2012 | Sonderegger |
| 2012/0310175 A1 | 12/2012 | Vedrine et al. |
| 2012/0323183 A1 | 12/2012 | Peterson et al. |
| 2013/0006195 A1 | 1/2013 | Sonderegger et al. |
| 2013/0046239 A1 | 2/2013 | Gonnelli et al. |
| 2013/0090625 A1 | 4/2013 | Moberg et al. |
| 2013/0226086 A1 | 8/2013 | Davies et al. |
| 2013/0253434 A1 | 9/2013 | Cabiri |
| 2013/0283196 A1 | 10/2013 | Farnan et al. |
| 2013/0289484 A1 | 10/2013 | Bazargan et al. |
| 2013/0332874 A1 | 12/2013 | Rosinko et al. |
| 2013/0338589 A1 | 12/2013 | Cindrich et al. |
| 2014/0025002 A1 | 1/2014 | Qi et al. |
| 2014/0035604 A1 | 2/2014 | Paul et al. |
| 2014/0046259 A1 | 2/2014 | Reber et al. |
| 2014/0052096 A1 | 2/2014 | Searle et al. |
| 2014/0088549 A1 | 3/2014 | Cole et al. |
| 2014/0100544 A1 | 4/2014 | Hwang |
| 2014/0114251 A1 | 4/2014 | Miyazaki |
| 2014/0114252 A1 | 4/2014 | Patel et al. |
| 2014/0121598 A1 | 5/2014 | Katase |
| 2014/0128815 A1 | 5/2014 | Cabiri et al. |
| 2014/0135694 A1 | 5/2014 | Moberg et al. |
| 2014/0135695 A1 | 5/2014 | Grant et al. |
| 2014/0142499 A1 | 5/2014 | Moberg et al. |
| 2014/0148784 A1 | 5/2014 | Anderson et al. |
| 2014/0180210 A1 | 6/2014 | Niklaus et al. |
| 2014/0207104 A1 | 7/2014 | Vouillamoz et al. |
| 2014/0207106 A1 | 7/2014 | Bechmann et al. |
| 2014/0207122 A1 | 7/2014 | Villegas et al. |
| 2014/0213975 A1 | 7/2014 | Clemente et al. |
| 2014/0221914 A1 | 8/2014 | Calasso |
| 2014/0221974 A1 | 8/2014 | Bechmann et al. |
| 2014/0243749 A1 | 8/2014 | Edwards et al. |
| 2014/0249500 A1 | 9/2014 | Estes |
| 2014/0276423 A1 | 9/2014 | Lecanu-Fayet |
| 2014/0296782 A1 | 10/2014 | Ulrich et al. |
| 2014/0296787 A1 | 10/2014 | Agard et al. |
| 2014/0330243 A1 | 11/2014 | Kietzmann et al. |
| 2014/0364808 A1 | 12/2014 | Niklaus et al. |
| 2014/0371675 A1 | 12/2014 | Hegland et al. |
| 2015/0005703 A1 | 1/2015 | Hutchinson et al. |
| 2015/0011939 A1 | 1/2015 | Marbet et al. |
| 2015/0011965 A1 | 1/2015 | Cabiri |
| 2015/0011973 A1 | 1/2015 | Edwards et al. |
| 2015/0011976 A1 | 1/2015 | Vouillamoz et al. |
| 2015/0018768 A1 | 1/2015 | Gray et al. |
| 2015/0025457 A1 | 1/2015 | Moberg et al. |
| 2015/0057615 A1 | 2/2015 | Mernoe, V et al. |
| 2015/0065958 A1 | 3/2015 | Teutsch et al. |
| 2015/0065959 A1 | 3/2015 | Carter et al. |
| 2015/0080799 A1 | 3/2015 | Schneider et al. |
| 2015/0080843 A1 | 3/2015 | Yodfat et al. |
| 2015/0094684 A1 | 4/2015 | Kriesel et al. |
| 2015/0133855 A1 | 5/2015 | Smith et al. |
| 2015/0151082 A1 | 6/2015 | Gescheit |
| 2015/0165113 A1 | 6/2015 | Lanigan et al. |
| 2015/0174324 A1 | 6/2015 | Wurmbauer et al. |

(56) References Cited

U.S. PATENT DOCUMENTS

| | | |
|---|---|---|
| 2015/0182688 A1 | 7/2015 | Dhami |
| 2015/0182689 A1 | 7/2015 | Dhami |
| 2015/0190574 A1 | 7/2015 | Gravesen et al. |
| 2015/0231328 A1 | 8/2015 | Mandro et al. |
| 2015/0265764 A1 | 9/2015 | Weber et al. |
| 2015/0273151 A1 | 10/2015 | McLoughlin et al. |
| 2015/0306307 A1 | 10/2015 | Cole et al. |

FOREIGN PATENT DOCUMENTS

| | | |
|---|---|---|
| JP | 2012-501771 A | 1/2012 |
| JP | 2013-519471 A | 5/2013 |
| JP | 2013-539684 A | 10/2013 |
| WO | WO-91/05867 A1 | 5/1991 |
| WO | WO-95/05465 A1 | 2/1995 |
| WO | WO-9638557 A1 | 12/1996 |
| WO | WO-9721457 A1 | 6/1997 |
| WO | WO-99/66054 A2 | 12/1999 |
| WO | WO-00/24893 A2 | 5/2000 |
| WO | WO-00/61637 A1 | 10/2000 |
| WO | WO-01/031007 A2 | 5/2001 |
| WO | WO-01/36489 A2 | 5/2001 |
| WO | WO-0181405 A2 | 11/2001 |
| WO | WO-0214356 A2 | 2/2002 |
| WO | WO-02/19963 A2 | 3/2002 |
| WO | WO-02/20034 A1 | 3/2002 |
| WO | WO-02/49673 A2 | 6/2002 |
| WO | WO-02/085940 A2 | 10/2002 |
| WO | WO-03/029291 A2 | 4/2003 |
| WO | WO-03/030833 A2 | 4/2003 |
| WO | WO-03/055526 A2 | 7/2003 |
| WO | WO-03/057134 A2 | 7/2003 |
| WO | WO-03/059951 A2 | 7/2003 |
| WO | WO-03/084477 A2 | 10/2003 |
| WO | WO-03/094858 A2 | 11/2003 |
| WO | WO-2004/002417 A2 | 1/2004 |
| WO | WO-2004/002424 A2 | 1/2004 |
| WO | WO-2004/009627 A1 | 1/2004 |
| WO | WO-2004/018667 A1 | 3/2004 |
| WO | WO-2004/024761 A1 | 3/2004 |
| WO | WO-2004/033651 A2 | 4/2004 |
| WO | WO-2004/035603 A2 | 4/2004 |
| WO | WO-2004/043382 A2 | 5/2004 |
| WO | WO-2004/058988 A2 | 7/2004 |
| WO | WO-2004/101600 A2 | 11/2004 |
| WO | WO-2004/101606 A2 | 11/2004 |
| WO | WO-2004/101611 A2 | 11/2004 |
| WO | WO-2004/106373 A1 | 12/2004 |
| WO | WO-2005/001025 A2 | 1/2005 |
| WO | WO-2005/001136 A1 | 1/2005 |
| WO | WO-2005/016970 A2 | 2/2005 |
| WO | WO-2005/017107 A2 | 2/2005 |
| WO | WO-2005/021579 A2 | 3/2005 |
| WO | WO-2005/025606 A1 | 3/2005 |
| WO | WO-2005/032460 A2 | 4/2005 |
| WO | WO-2005/047331 A2 | 5/2005 |
| WO | WO-2005/051327 A2 | 6/2005 |
| WO | WO-2005/058967 A2 | 6/2005 |
| WO | WO-2005/063808 A1 | 7/2005 |
| WO | WO-2005/063809 A1 | 7/2005 |
| WO | WO-2005/070451 A1 | 8/2005 |
| WO | WO-2005/081687 A2 | 9/2005 |
| WO | WO-2005/084711 A1 | 9/2005 |
| WO | WO-2005/092369 A2 | 10/2005 |
| WO | WO-2005/100403 A2 | 10/2005 |
| WO | WO-2005/103076 A2 | 11/2005 |
| WO | WO-2006/02646 A2 | 1/2006 |
| WO | WO-2006/013472 A2 | 2/2006 |
| WO | WO-2006/29094 A2 | 3/2006 |
| WO | WO-2006/50959 A2 | 5/2006 |
| WO | WO-2006/069202 A2 | 6/2006 |
| WO | WO-2006081171 A1 | 8/2006 |
| WO | WO-2006/138729 A2 | 12/2006 |
| WO | WO-2007/000328 A1 | 1/2007 |
| WO | WO-2007/011941 A2 | 1/2007 |
| WO | WO-2007/012614 A2 | 2/2007 |
| WO | WO-2008/057457 A2 | 5/2008 |
| WO | WO-2008/057458 A2 | 5/2008 |
| WO | WO-2008/057459 A2 | 5/2008 |
| WO | WO-2008/063382 A2 | 5/2008 |
| WO | WO-2008/125623 A2 | 10/2008 |
| WO | WO-2008/133647 A2 | 11/2008 |
| WO | WO-2009/055783 A2 | 4/2009 |
| WO | WO-2009/100297 A1 | 8/2009 |
| WO | WO-2009/100318 A1 | 8/2009 |
| WO | WO-2010018411 A1 | 2/2010 |
| WO | WO-2010/029513 A2 | 3/2010 |
| WO | WO-2010/077854 A1 | 7/2010 |
| WO | WO-2011/037791 A1 | 3/2011 |
| WO | WO-2011036294 A1 | 3/2011 |
| WO | WO-2011/053759 A1 | 5/2011 |
| WO | WO-2011/053783 A2 | 5/2011 |
| WO | WO-2011/072263 A1 | 6/2011 |
| WO | WO-2011/101375 A1 | 8/2011 |
| WO | WO-2011/111007 A2 | 9/2011 |
| WO | WO-2012032411 A2 | 3/2012 |
| WO | WO-2012/045836 A2 | 4/2012 |
| WO | WO-2012/054438 A1 | 4/2012 |
| WO | WO-2012/088313 A1 | 6/2012 |
| WO | WO-2012/101251 A1 | 8/2012 |
| WO | WO-2012/101252 A2 | 8/2012 |
| WO | WO-2012/101253 A1 | 8/2012 |
| WO | WO-2012/109530 A1 | 8/2012 |
| WO | WO-2013/075773 A2 | 5/2013 |
| WO | WO-2014066256 A1 | 5/2014 |
| WO | WO-2014116998 A2 | 7/2014 |

OTHER PUBLICATIONS

International Search Report for PCT/US2015/064869 dated Mar. 17, 2016.

Written Opinion of the International Searching Authority, International Application PCT/US2015/064869, dated Jun. 23, 2016.

Lu et al., Simultaneous blockade of both the epidermal growth factor receptor and the insulin-like growth factor receptor signaling pathways in cancer cells with a fully human recombinant bispecific antibody, J. Biol. Chem., 279(4):2856-65 (2004).

Maloney et al., An anti-insulin-like growth factor I receptor antibody that is a potent inhibitor of cancer cell proliferation, Cancer Res., 63(16):5073-83 (2003).

Cohen et al., Combination therapy enhances the inhibition of tumor growth with the fully human anti-type 1 insulin-like growth factor receptor monoclonal antibody CP-751,871, Clin. Cancer Res., 11(5):2063-73 (2005).

Varghese et al., Oncolytic herpes simplex virus vectors for cancer virotherapy, Cancer Gene Ther., 9(12):967-78 (2002).

Liu et al., Preclinical evaluation of herpes simplex virus armed with granulocyte-macrophage colony-stimulating factor in pancreatic carcinoma, World J. Gastroenterology, 19:5138-43 (2013).

Partial International Search Report for application No. PCT/US2015/066597, dated Mar. 29, 2016.

International Search Report for PCT/US2015/066597, dated Jun. 9, 2016.

Written Opinion of the International Searching Authority, for International Application PCT/US2015/066597, dated Jun. 23, 2016.

U.S. Appl. No. 15/047,853, Nonfinal Office Action, dated Jun. 26, 2019.

U.S. Appl. No. 15/522,345, Nonfinal Office Action, dated Jul. 19, 2019.

European Patent Application No. 15817689.1, Communication Pursuant to Article 94(3) EPC, dated Oct. 26, 2018.

International Preliminary Report on Patentability and Written Opinion of International Application No. PCT/US2015/066597, dated Jun. 20, 2017.

Japanese Patent Application No. 2017-532785, Notice of Rejection, dated Jul. 31, 2018.

Japanese Patent Application No. 2017-532785, Second Official Action, dated Mar. 5, 2019.

U.S. Appl. No. 15/047,853, Advisory Action, dated Mar. 20, 2019.

U.S. Appl. No. 15/047,853, Final Office Action, dated Dec. 6, 2018.

(56) References Cited

OTHER PUBLICATIONS

U.S. Appl. No. 15/047,853, Nonfinal Office Action, dated May 16, 2018.
European Patent Application No. 15820801.7, Communication Pursuant to Article 94(3) EPC, dated May 27, 2020.
European Patent Application No. 20160603.5, Extended European Search Report, dated May 13, 2020.
Japanese Patent Application No. 2017-532778, Notice of Rejection, dated Aug. 20, 2019.
U.S. Appl. No. 15/040,361, Final Office Action, dated Jun. 26, 2020.
U.S. Appl. No. 15/040,361, Nonfinal Office Action, dated Jan. 6, 2020.
U.S. Appl. No. 15/047,853, Final Office Action, dated Jan. 7, 2020.
U.S. Appl. No. 15/522,345, Final Office Action, dated Jan. 21, 2020.
Japanese Patent Application No. 2020-032832, Office Action, dated Mar. 2, 2021.
Japanese Patent Application No. 2020-032832, Decision of Rejection, dated Nov. 30, 2021.

* cited by examiner

DRUG DELIVERY DEVICE WITH LIVE BUTTON OR USER INTERFACE FIELD

CROSS-REFERENCE TO RELATED APPLICATIONS

This is the United States national phase of International Patent Application No. PCT/US2015/064869, with an international filing date of Dec. 10, 2015, which claims the priority benefit of U.S. Provisional Application No. 62/094,516, filed Dec. 19, 2014, the entire contents of each of the foregoing is expressly incorporated herein by reference.

FIELD OF THE DISCLOSURE

The present disclosure relates to drug delivery devices. More particularly, the present disclosure relates to drug delivery devices, which have an activation button or user interface that indicates when the device is ready to deliver or inject and suggests the next step in the delivery or injection process.

BACKGROUND

Drug delivery devices, such as on-body injectors and hand-held injectors, are well known in the art. Such drug delivery devices may be constructed as single use or reusable devices and may include components which allow automatic operation of the device.

On-body and hand-held injectors may be commonly prescribed for patients to self-administer medication, typically offering a preferred injector type based on patient population and therapeutic needs. These injection devices can offer a compelling improvement to outcomes beyond a vial or prefilled syringe due to their ease of use and what may typically be considered a less intimidating injection process, among other factors.

It may be desirable to assist a patient in the self-administration of a prescribed medication. Unfortunately, on-body and/or hand-held injectors may appear complicated or intimidating to patients that are not familiar with them. On-body injectors, for example, may have operational steps including without limitation one or more of site preparation, unpackaging, adhesive liner removal, medication transfer, application to the body, injection, removal, and disposal.

One of the opportunities to improve these injectors may be to clarify when the device is "ready to go" or "ready to inject" while simultaneously highlighting the next step in the process.

Accordingly, a drug delivery device is needed, which clarifies or indicates when the device is ready to go or inject while simultaneously highlighting the next step in the drug administration process.

SUMMARY

Disclosed herein is a drug delivery device, a method of preparing a drug delivery device, and a method of using a drug delivery device. Various embodiments of the drug delivery device may comprise a container for storing a drug, the container comprising a stopper for expelling the drug; an injection drive comprising an energy source for acting directly or indirectly on the stopper to expel the drug; a sensor for detecting contact between the drug delivery device and a body of a patient; and a user interface (UI) for activating or causing the activation of the injection drive; wherein attention is drawn to the UI by effecting an external state change of the UI, if the sensor detects contact between the drug delivery device and the body of the patient, thereby indicating that the injection drive is ready to be activated.

BRIEF DESCRIPTION OF THE DRAWINGS

The same reference numerals are used in the drawings to identify the same or similar elements and structures in the various embodiments.

GENERAL DESCRIPTION

Figure 1A:
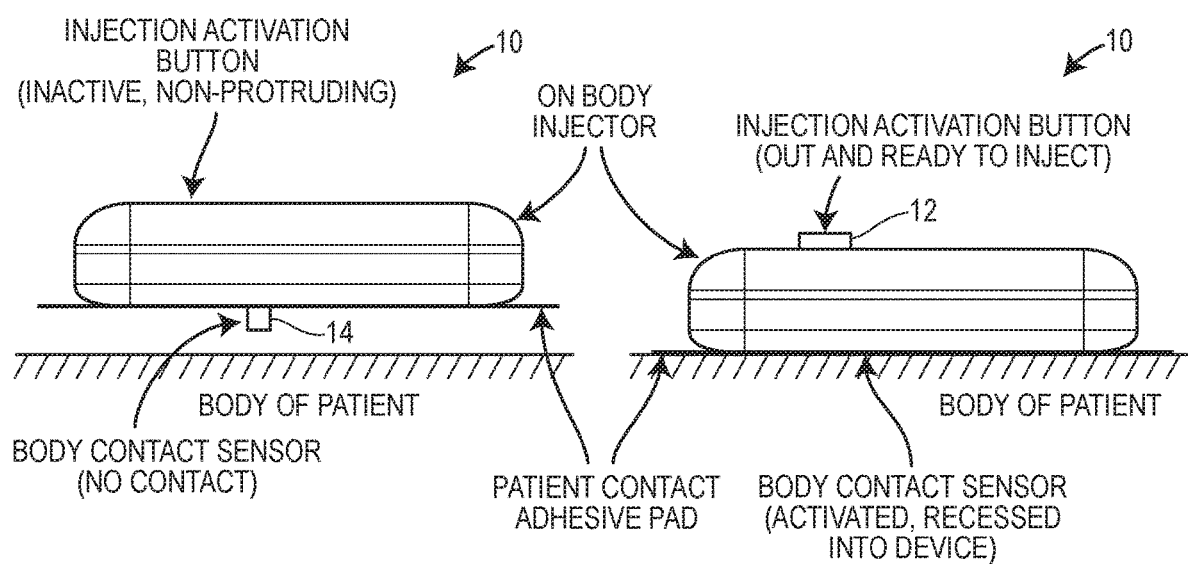
FIG. 1A is an elevational view of an on-body drug delivery device according to an embodiment of the disclosure.

Disclosed herein is a drug delivery device that includes a container, an injection drive, a sensor and a device activation mechanism. The container is for storing a drug, and can have a stopper for expelling the drug. The injection drive can include an energy source operably coupled to the stopper for selectively moving the stopper through the container to expel the drug. The sensor can have a first state when the drug delivery device is out of contact with a body of a patient, and a second state when the drug delivery device is in contact with the body of the patient. The device activation mechanism can be operably coupled to the sensor and the injection drive for selectively activating the injection drive in response to user input. The device activation mechanism can undergo an external state change from a dormant state, when the sensor occupies the first state, to a ready state, upon the sensor occupying the second state, the ready state drawing attention to the device activation member.

Also disclosed herein is a drug delivery device for drug delivery, which in various embodiments comprises a container, an injection drive, a sensor, and a user interface. The container may have a stopper for expelling a drug stored in the container. The injection drive may comprise an energy source for expelling the drug. The sensor detects contact between the drug delivery device and a body of a patient and the user interface activates or causes activation of the injection drive. Attention is drawn to the user interface, if the sensor detects contact between the drug delivery device and the body of the patient, thereby indicating that the injection drive is ready to be activated.

Further disclosed herein is a method for administering a drug, which in various embodiments comprises providing a container for storing a drug, the container comprising a stopper for expelling the drug; providing an injection drive comprising an energy source for directly or indirectly acting on the stopper to expel the drug; providing a start member for activating the injection drive; detecting contact between the drug delivery device and a body of a patient with a sensor; drawing attention to the start member, if the sensor detects contact between the drug delivery device and the body of the patient, thereby indicating that the injection drive is ready to be activated; and activating the injection drive with the start member after the attention has been drawn to the start member.

Further disclosed herein is a method of preparing a drug delivery device to deliver a drug, which can include providing a drug delivery device that has a container, an injection drive, a sensor and a device activation mechanism. The container is for storing a drug, and has a stopper for expelling the drug. The injection drive includes an energy source operably coupled to the stopper for selectively moving the stopper through the container to expel the drug. The device activation mechanism is operably coupled to the sensor and the injection drive. The method further includes detecting contact between the drug delivery device and an injection site with the sensor, causing the sensor to change from a first state to a second state. Then, when the sensor occupies the second state, the method includes delivering contact information to the device activation mechanism with the sensor, the contact information indicative of the relationship between the drug delivery device and the injection site. Then, upon receiving the contact information, the method includes causing a physical appearance of at least a portion of the device activation mechanism to change from a dormant state to a ready state, thereby drawing attention to the device activation mechanism to signal to a user that the drug delivery device is ready for use.

DETAILED DESCRIPTION

Figure 1B:
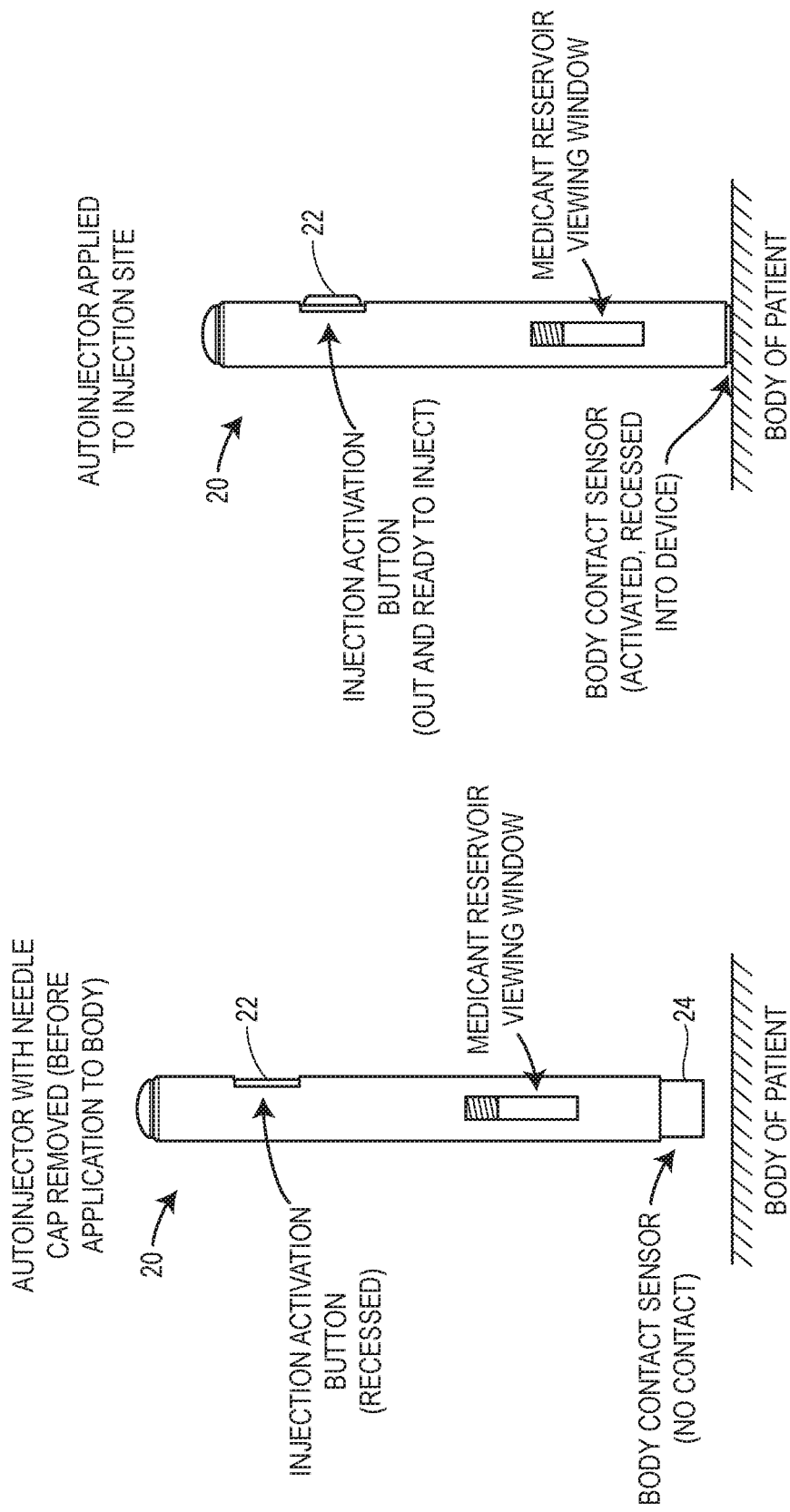
FIG. 1B is an elevational view of a hand-held drug delivery device according to an embodiment of the disclosure.

Referring now to FIGS. 1A and 1B, the drug delivery device may comprise a reusable or disposable injector or autoinjector which automatically delivers a subcutaneous injection of a fixed or user/patient-settable dose of a drug. As illustrated in FIG. 1A, various embodiments of the drug delivery device may be configured as an on-body injection device or injector 10 that attaches to the body of the patient and automatically delivers the drug over a controlled or predetermined period of time (e.g., from 30 seconds up to one or more hours). In various other embodiments, as illustrated in FIG. 1B, the drug delivery device may be configured as a hand-held injection device or injector 20 that is placed momentarily against the body of the patient and automatically delivers the drug over a relatively short period of time (e.g., less than 10 seconds). Such drug delivery devices are intended for self-administration (patient), but can of course be used by a caregiver or a formally trained healthcare provider (operator) to administer an injection.

Referring again to FIGS. 1A and 1B, the injection device 10, 20 may be configured to draw the patient's or operator's attention to a user interface (UI) such as a button-type actuator 12, 22, after a body contact sensor 14, 24 detects contact between the injection device 10, 20 and the body of the patient, to signal or indicate that the injection device 10, 20 is ready to be activated via the UI 12, 22, which is the next step in the injection process. In some embodiments, readiness can be signaled/indicated by effecting an external state change such as but not limited to motion, sound, light, colors, and any combination thereof. For example, in the embodiments shown in FIGS. 1A and 1B, the external state change comprises the raising or "popping out" of the actuator 12, 22. In other embodiments, the external state change can comprise without limitation rotating the actuator, illuminating the actuator, changing the color of the actuator, revealing the actuator, generating a sound, generating a vibration, and any combination thereof. The placement of the injection device against the body of the patient in various embodiments may unlock the UI and/or the device activation mechanism and cause the external state change which calls attention to the UI. In various embodiments, the signal/indication and the unlocking UI and/or device activation mechanism can occur at approximately the same time. In other embodiments, the pre-application state of the device (device not engaged with the body of the patient) may lock UI and/or the device activation mechanism such that the operation of signal/indication function unlocks the UI and/or the device activation mechanism.

In various other embodiments, the removal of the device from the body of the patient without activation may lockout the UI and/or activation mechanism and return the UI to the original state (e.g., lower or conceal the actuator, turn off the illumination, sound, vibration, and any combination thereof,). In such embodiments, the re-placement of the device against the body of the patient may unlock the UI and/or device activation mechanism and cause the external state change, which calls attention to the UI.

Figure 2A:
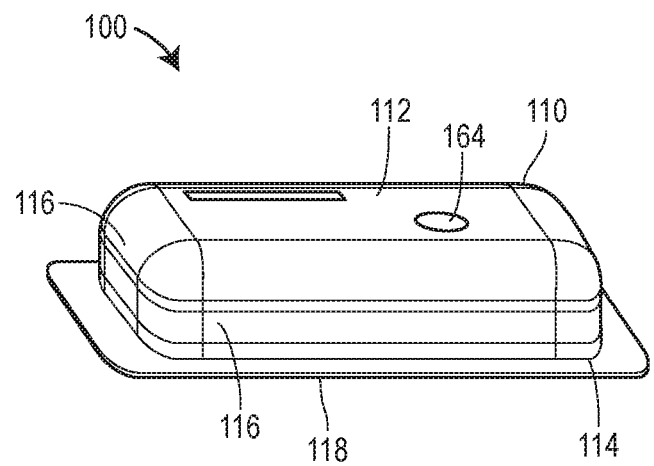
FIG. 2A is perspective view showing the top of an on-body drug injection device according to an embodiment of the disclosure.
Figure 2B:
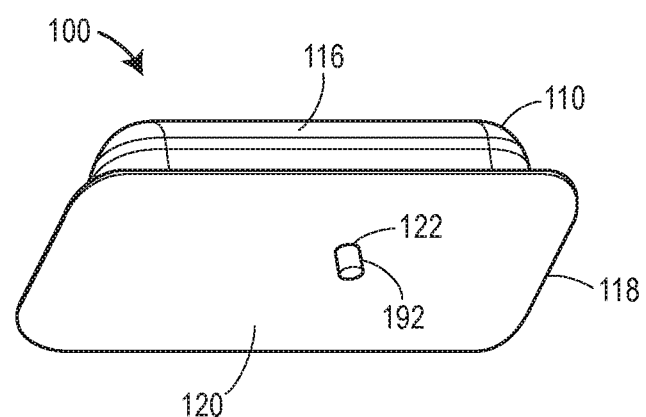
FIG. 2B is perspective view showing the bottom of the on-body drug injection device of FIG. 2A.

FIGS. 2A-2D collectively illustrate an embodiment of an on-body injection device 100 according to the present disclosure. The device 100 comprises an outer casing 110, which can have a top wall 112, a base or bottom wall 114, and one or more side walls 116 that extend between the top and bottom walls 112, 114. The top or side walls 112, 114 of the casing 110 (top wall 112 as shown in FIG. 2A) may include a UI 164 which allows the patient or operator to activate the device 100. As shown in FIG. 2B, the injection device 100 may further comprise an adhesive pad 118 or any other suitable arrangement or mechanism for removably attaching the device 100 to the body B of the patient. The adhesive pad 118 may substantially cover the entire bottom wall 114 of the casing 110 or one or more selected portions of the bottom wall 114. A removable sterile barrier film (not shown) may be provided for covering the adhesive pad 118 prior to use of the device 100. The bottom wall 114 of the casing 110 and the adhesive pad 118 can include a first pair of coaxially aligned openings 120 which allow an injection needle 138 (FIGS. 2C and 3B) or any other suitable drug delivery member, element, or device, to extend out from the device casing 110 during the injection process to penetrate the body B (e.g., skin) of the patient. A depressible body sensing pin 192 or other depressible or deflectable member of an electromechanical body contact sensor 190, may extend through a second pair of coaxially aligned openings 122 defined in the bottom wall 114 of the casing 110 and the adhesive pad 118. The body sensing pin 192 or deflectable member may be depressible or deflectable in a linear, rotational, or compressive manner. The body contact sensor 190 may include a sensor that changes from a first state to a second state upon contacting an injection site such as a patient's body and may be capable of communicating sensor information to the device activation mechanism 160 through a central processing unit 194, a mechanical linkage, or otherwise. Electromechanical sensors may include switches and the like for monitoring the movement of the pin or other depressible or deflectable member as it is depressed or deflected during the body sensing process. Compressive depressible and deflectable members may be implemented with a compressible pad. Such sensors may use capacitive or resistive methods to detect pad compression. In various other embodiments, the body contact sensor 190 may comprise an electrical sensor, such as but not limited to a capacitive sensing device, an impedance sensor, or a proximity sensor, such as but not limited to an infrared proximity or distance sensor, which do not use depressible or deflectable pins or other members. In still further embodiments, the body contact sensor 190 may comprise a purely mechanical sensor or an optical sensor for sensing contact between the device 100 and the body B of the patient and changing from a first state to a second state upon said contact.

Figure 2C:
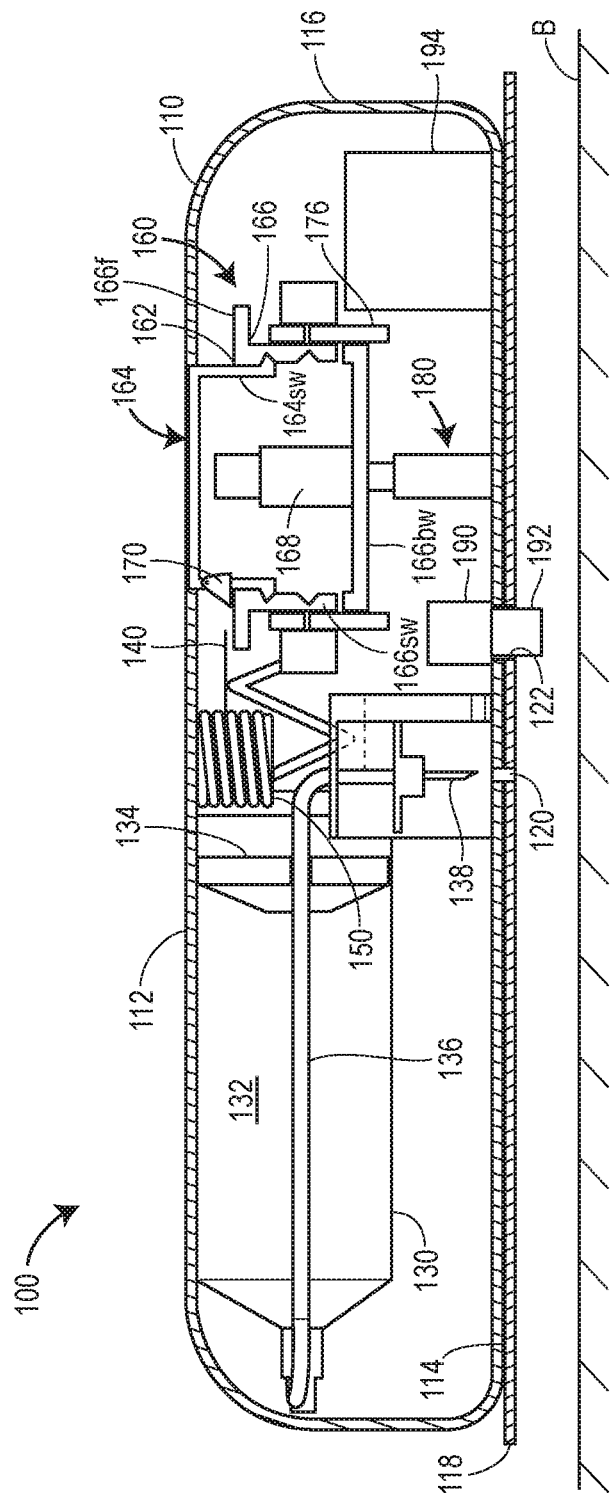
FIG. 2C is an elevational view with certain elements shown in cross-section of the on-body injection device of FIGS. 2A and 2B.

As shown in FIG. 2C, the on-body injection device 100 may further comprise a medicament container 130 for storing a drug to be administered to a patient, an injection drive comprising a stopper drive 140 and/or a needle insertion drive 150, a device activation mechanism 160 and switch lifting mechanism 180. The casing 110 in reusable embodiments of the device 100 may be configured to allow removal and insertion of the medicant container 140. For example, in some embodiments of the device 100, the casing 110 may have a closure (not shown) that allows insertion and removal of the medicament container 130. In other embodiments of the device 100, the casing 110 may configured so that the bottom wall 114 can be removed from the rest of the casing 110 to allow insertion and removal of the medicament container 130.

In various embodiments, the medicament container 130 may be pre-filled with the drug 132. A stopper 134 may be movably disposed within the medicament container 130 for expelling the drug 132 from the container 130. A tube 136 may be provided for fluid coupling the medicament container 130 to a remotely located injection needle 138, thereby allowing the drug 132 to be expelled from the container 130 and dispensed by the injection needle 138

The stopper drive 140 acts on the stopper 134 to move it through the medicament container 130 to expel the drug 132 therefrom. In various embodiments, the stopper drive 140 may comprise a plunger and an energy source for propelling the plunger. The energy source may comprise a mechanical arrangement of one or more springs or an electrical/mechanical arrangement comprising one or more motors and/or solenoids and a drive train or transmission, or an arrangement that generates or releases a pressurized gas or fluid. In other embodiments, the stopper drive may comprise an arrangement that generates or releases a pressurized gas or fluid which acts directly on the stopper to move the stopper through the medicament container 130.

Figure 3A:
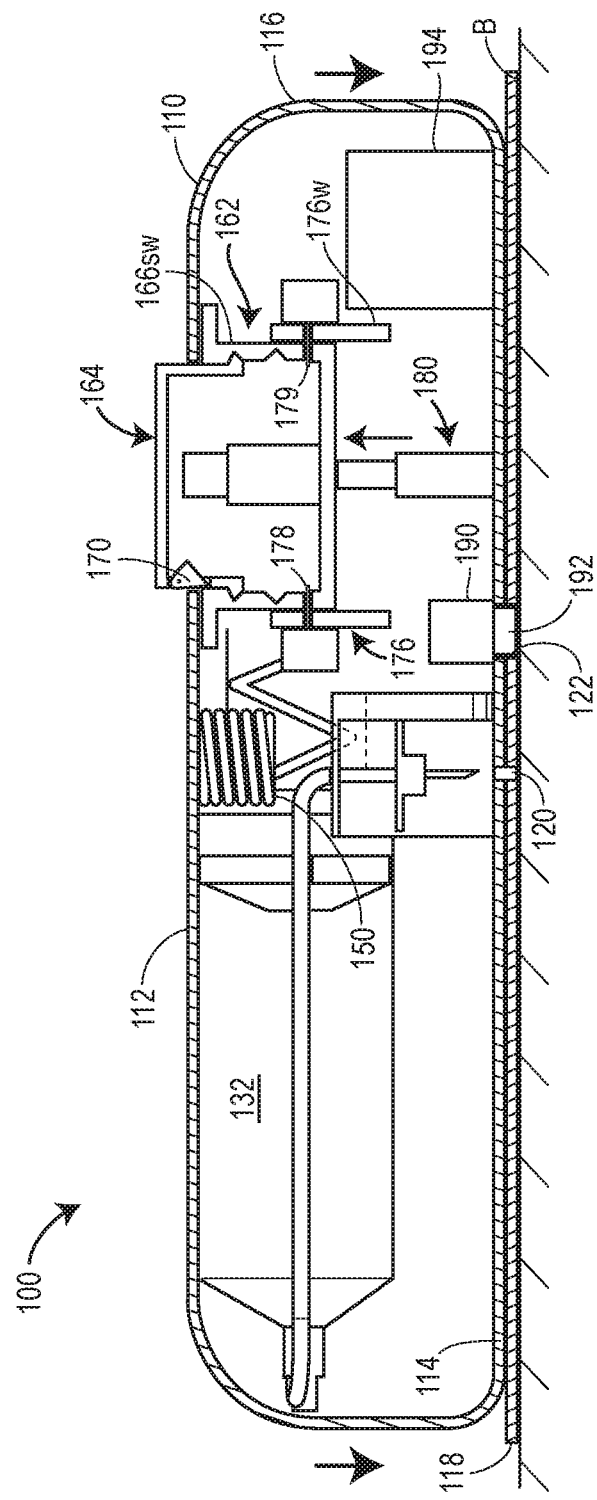
FIGS. 3A and 3B are elevational views with certain elements shown in cross-section, illustrating the operation of the on-body injection device of FIGS. 2A-2D.
Figure 3B:
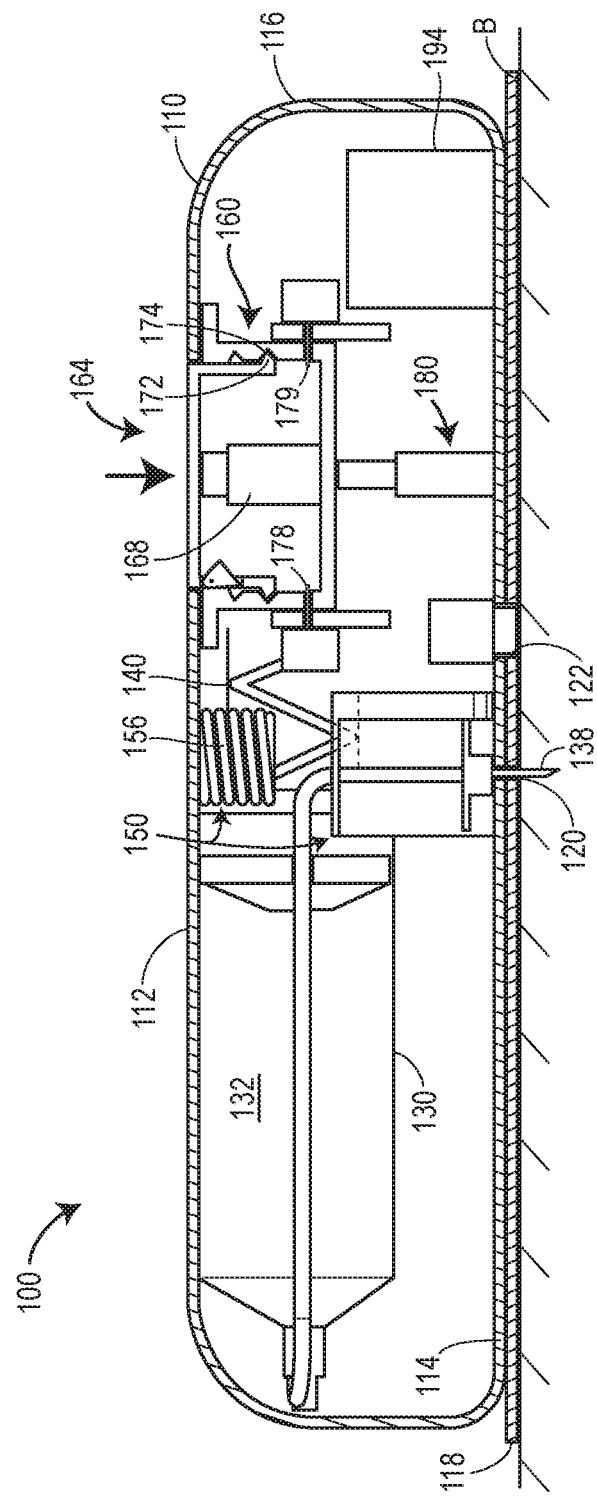
Figure 4A:
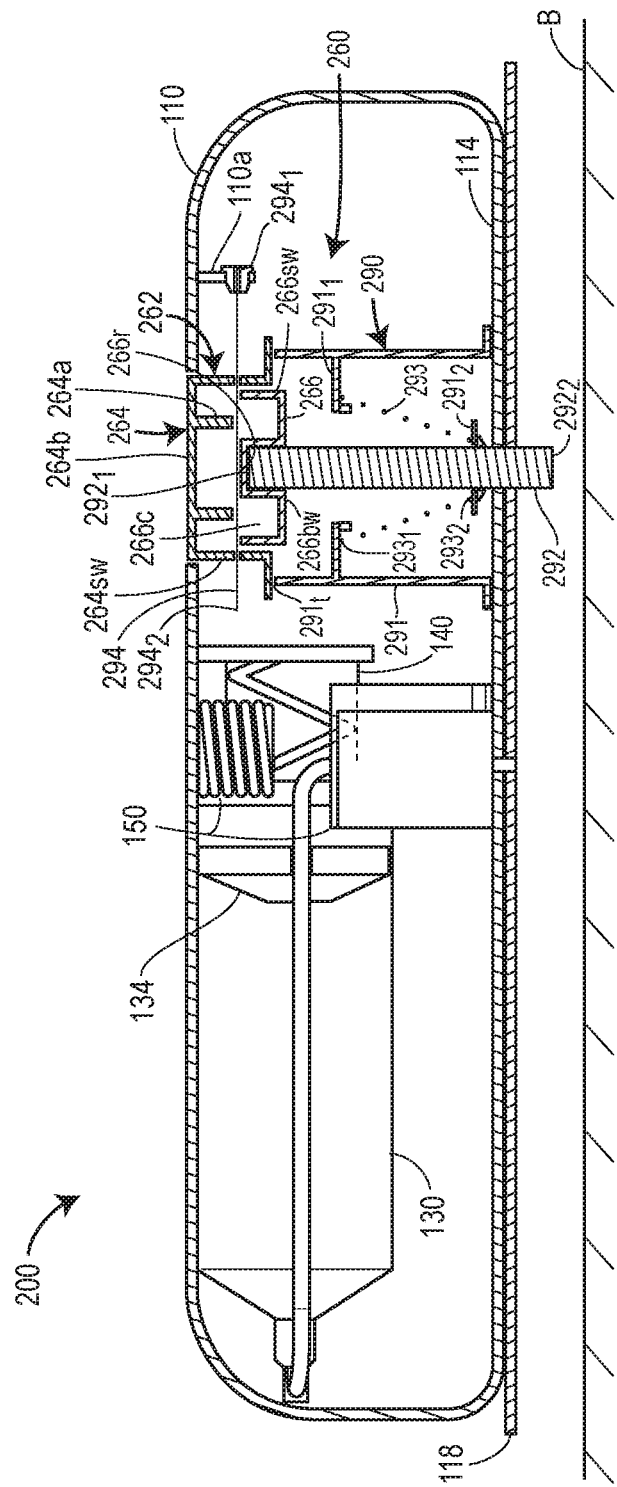
FIG. 4A is an elevational view with certain elements shown in cross-section of an on-body injection device according to another embodiment of the disclosure.
Figure 4B:
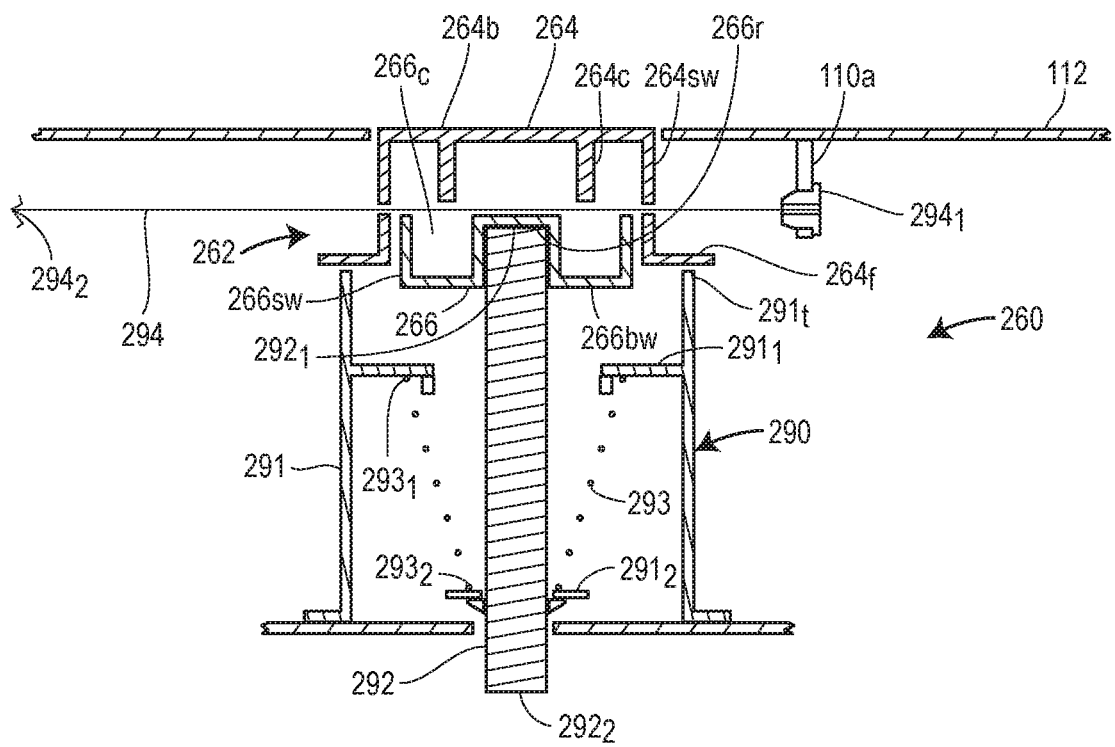
FIG. 4B is an enlarged elevational view of a device activation mechanism illustrated in FIG. 4A.

The needle insertion drive 150 may be configured to move the injection needle 138 between first and second positions. In the first position, the injection needle 138 may be disposed entirely within the interior of the casing 110 and concealed from view as shown in FIG. 3A. In the second position, at least a portion of the injection needle 138 may extend out through the openings 122 in the bottom wall 114 of the casing 110 and adhesive pad 118, as shown in FIG. 3B.

The CPU 194 or like device may be housed in the casing 110 or located remotely from the device 100. The CPU 194, the device activation mechanism 160 and the body contact sensor 190 may operate together to activate, deactivate, and/or control the stopper drive 140 and/or needle insertion drive 150. In some embodiments, the CPU 194 may control the stopper drive 140 so that the device 100 administers the drug to the patient at a controlled rate. The CPU 194 may also be configured to allow the patient or operator to set the drug administration rate of the device 100. In other embodiments, the CPU 194 can be configured to control the activation sequence and/or deactivation sequence of the stopper drive 140 and the needle insertion drive 150.

Figure 2D:
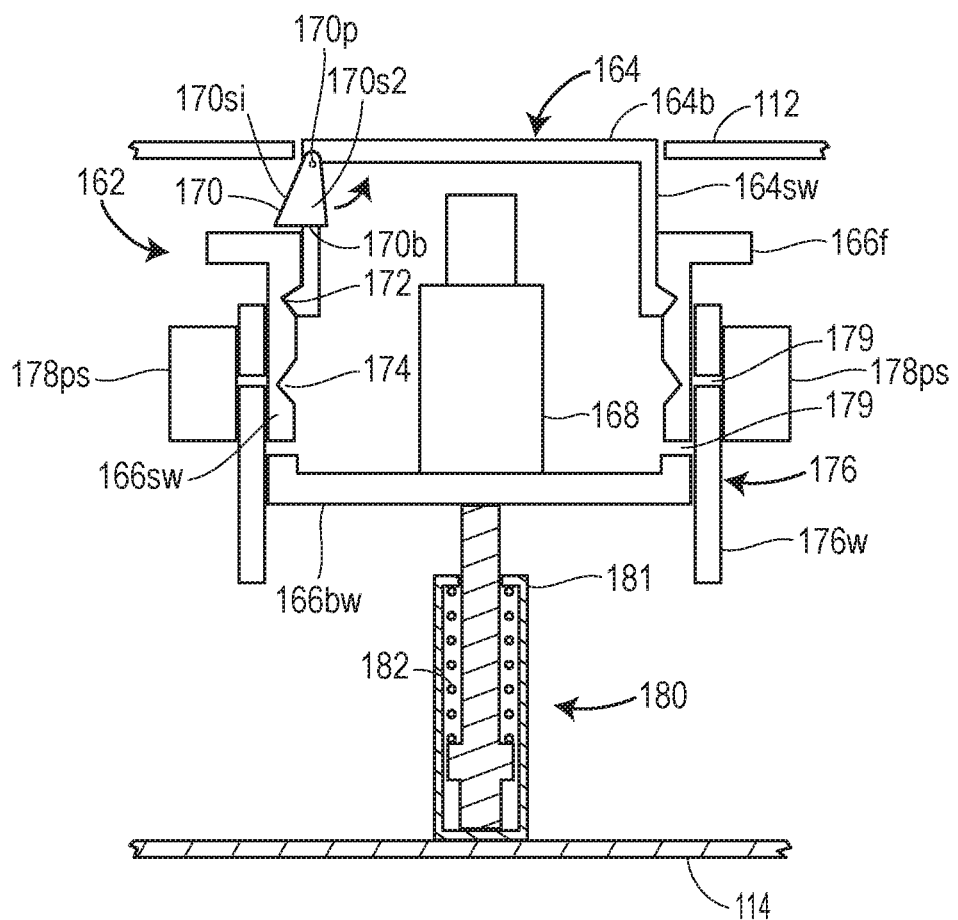
FIG. 2D is an enlarged elevational view of an embodiment of a device activation mechanism illustrated in FIG. 2C.

The device activation mechanism 160 initiates, triggers, or activates the device 100 in response to a patient or operator input at the UI 164. As shown in FIGS. 2C and 2D, the UI 164 and the device activation mechanism 160 may be integrated into a single component comprising an electromechanical switch assembly 162 where the UI 164 is implemented as a depressible actuator. In other embodiments, the UI and device activation mechanism may be separate, operatively connected components. The device activation mechanism 160 communicates switching information to the CPU 194, which in response, activates one or both of the needle insertion drive 150 and stopper drive 140.

Referring still to FIG. 2C and FIG. 2D, the switch lifting mechanism 180 (switch lift) may be mounted on the bottom wall 114 of the device casing 110, for changing the external state of the device activation mechanism 160. Specifically, the switch lift 180 is for raising the switch assembly 162 of the device activation mechanism 160 from a dormant state (i.e., a lowered position) as shown to a ready state (i.e., a raised position) within the casing 100 (FIG. 3A) when the device 100 is properly engaged or in contact with the body B of the patient to bring attention to the UI/actuator 164. The switch assembly 162 may include a latch 170 which unlocks the UI/actuator 164 and therefore, the device activation mechanism 160. The switch assembly 162 may ride in a guide channel 176 formed within the device casing 100, as it is raised and lowered by the switch lift 180. The CPU 194 controls the switch lift 180 based on signals the CPU 194 receives from the body contact sensor 190. Specifically, if the body contact sensor 190 sends a signal indicating that the device 100 is properly engaged with the body B of the patient, and therefore occupying the second state, the CPU 194 can send a signal to the switch lift 180 which causes it to raise the switch assembly 162 from the formant state to the ready state. This changes in outward appearance of the device activation mechanism 160 by causing the switch assembly 262 to prominently protrude out of the drug delivery device 100. If after raising the switch assembly 162 and prior to the patient activating the device 100 via the UI/actuator 164, the CPU 194 receives another signal from the body contact sensor 190 that the device activation mechanism 160 has partially or completely disengaged from the body B of the patient, therefore occupying the first state, the CPU 194 can cause the switch lift 180 to lower the switch assembly 162, thereby re-locking the UI/actuator and the device activation mechanism 160.

In addition to the depressible UI/actuator 164, the electromechanical switch assembly 162 may further comprise a switch housing 166 and an activation switch 168 disposed in the switch housing 166. The UI/actuator 164 may telescopically move relative to the switch housing 166 between first (undepressed) and second (depressed) positions. The UI/actuator 164 may be flush with or recessed from the casing 110 (e.g., top wall 112) when the device 100 is in a not-ready-to-inject state, which is also referred to herein as the dormant state, i.e., where the switch assembly 162 is in the lowered position and the UI/actuator 164 is in the undepressed position. The latch 170 can be rotatively coupled to the UI/actuator 164 for locking the UI/actuator 164 in the first position if the switch assembly 162 is in a lower position (i.e., dormant state or not-ready-to-inject state) within the device casing 110.

As best illustrated in FIG. 2D, the switch housing 166 may have a cup-like structure formed by a cylindrical side wall 166*sw*, a base wall 166*bw* closing a bottom end of the side wall 166*sw* and an outwardly extending flange 166*f* disposed at the open top end of the side wall 166*sw*. The UI/actuator 164 may have a plug-like structure formed by a button member 164*b* and a resilient side wall 164*sw* depending from perimeter of the button member 164*b*. The latch 170 may comprise a planar, triangular structure comprising a base edge surface 170*b*, a convex first side edge surface 170*si*, and a flat second side edge surface 170*s*2, and a pivot pin 170*p* disposed or formed at the intersection of the first and second side edge surfaces 170*si*, 170*s*2. The pivot pin 170*o* rotatively mounts the latch 170 within a slot 164*s*1 formed in the side wall 164*sw* of UI/actuator 164, adjacent to or at a top end thereof. When the injection device 100 is in the dormant state where the switch assembly 162 is in the lower position and the UI/actuator 164 is in the first, undepressed position, the latch 170 is free to rotate down so that the base edge 170*b* surface faces the flange 166*f* of the switch housing 166, thereby locking the UI/actuator 164 so it cannot be depressed. A detent arrangement may be provided for setting the first and second positions of UI/actuator 164 in the switch housing 166. The detent arrangement may comprise a protruding catch element 172 formed on the outer surface of the UI/actuator side wall 164*sw* or the inner surface of the switch housing side wall 166*sw* and a pair of notches 174 formed on the other one of the UI/actuator side wall 164*sw* and switch housing side wall 166*sw*. The activation switch 168 may be mounted on the base wall 166*bw* of the switch housing 166 below the UI/actuator 164. The activation switch 168 may comprise an electromechanical switch or any other suitable switch capable of communicating switching information to the CPU such as but not limited to a capacitive, inductive or touch-sensitive switch.

As described earlier, the switch assembly 162 can be raised or lowered between the dormant and ready states in the guide channel 176. One or more locking pins 178 (FIG. 3B) may be provided for locking the switch assembly 162 in the raised position. The one or more locking pins 178 may extend through openings 179 in the guide channel 176*w* and the side wall of the switch housing 166 which align with one another when the switch assembly 162 is in the raised position. In various embodiments the locking pins 178 may be implemented with pin solenoids 178*ps*, as illustrated in FIG. 2D. In various other embodiments, the pins 178 may be biased toward the switch assembly 162 by a biasing member, such as but not limited to a spring (not shown).

The switch lift 180 may comprise without limitation a linear actuator or an electrical solenoid 181, mounted on the bottom wall 114 of the casing 110 below the switch housing 166 and a biasing member 182. In some embodiments, the actuator or solenoid 181 may be configured to raise the switch assembly 162 from the lowered position (FIGS. 2C and 2D) into the raised position (FIGS. 3B and 3C), and the biasing member 182 may be configured to bias the switch assembly 162 toward the lowered position so that when the actuator or solenoid 181 is deactivated, the biasing member 182 maintains the switch assembly 162 in the lowered position or returns the switch assembly 162 from the raised position to the lowered position. In such embodiments, the biasing member 182 may comprise but is not limited to an extension spring.

In other embodiments, the actuator or solenoid 181 may be configured to maintain the switch assembly 162 in the lowered position or to lower the switch assembly 162 to the lowered position from the raised position, and the biasing member 182 may be configured to raise the switch assembly 162 from the lowered position to the raised position. In such embodiments, the biasing member 182 may comprise but is not limited to a compression spring.

FIGS. 3A and 3B illustrate the external state change features of the injection device 100 of FIGS. 2A-2D. FIG. 3A, illustrates the injection device 100 after it has been properly placed in contact with the body B of a patient during the device mounting process. As the device 100 is mounted to the body B, the body contact information sensed by the sensing pin 192 of the body contact sensor 190 retracting from the first state to the second state is communicated to the CPU 194. In response to the body contact information, the CPU 194 activates the switch lift 180 to raise the switch assembly 162, which causes the UI/actuator 164 to rise or "pop out" of the device casing 110 and into the ready state, thereby drawing the patient's or operator's attention to the UI/actuator 164. The UI/actuator 164 may now be disposed above the exterior surface (e.g., top wall 112) of the casing 110, as shown in FIG. 3A, or in some other position relative to the casing 110. Once in the switch assembly 162 is in the ready state, it occupies the raised position and the locking pins 178 enter the openings 179 in the wall 176*w* of the guide channel 176 and side wall 166*sw* the switch housing 166 to lock the switch assembly 162 in the raised position. As the switch assembly 162 rises, the latch 170 engages the interior surface of the casing 110 (e.g., top wall 112) and rotates and unlocks the UI/actuator 164, which places the injection device 100 in the ready state, which can also be referred to as the ready-to-inject state. The motion or change in state of the UI/actuator 164, thus, signals to the patient or operator that the next step in the injection administering process is to depress UI/actuator 164.

FIG. 3B illustrates the injection device 100 after the patient or operator has depressed the UI/actuator 164 and moved it from the first undepressed position to the second depressed position as set by the detent arrangement 172, 174. As the UI/actuator 164 enters the second depressed position it engages or otherwise activates the activation switch 168. Once activated, the activation switch 168 communicates the switching information to the CPU 194. In response, the switching information, the CPU 194 activates the needle insertion drive 150 to drive the injection needle 138 in the body B of the patient and the stopper drive 140, which expels the drug 132 stored in the medicament container 130 through the injection needle 138 and into the patient's body B.

FIGS. 4A-4D collectively illustrate another embodiment of the on-body drug injection device 200. The device 200 is similar to the device 100 shown in FIGS. 2A-2D and 3A-3B, except that the device activation mechanism 260 comprises a UI/actuator 264 integrated into a mechanical switch assembly 262 and a mechanical body contact sensor 290 that also functions as a switch lift. As can be seen, the user mechanical switch assembly 262 may be directly coupled to a sensing pin 292 of the mechanical body contact sensor 290. The mechanical body contact sensor can be mounted, for example, on the bottom wall 114 of the device casing 110. In other embodiments, the UI/mechanical switch assembly may be coupled to the sensing pin of the mechanical body contact sensor by a linkage or other mechanism (not shown).

The sensing pin 292 of the body contact sensor 290 may include a first end 2921 which acts on the switch assembly 262 and a second end 2922 which contacts the body B of the patient when the device 200 is mounted thereon. In addition to the sensing pin 292, the mechanical body contact sensor 290 can comprise a housing 291 which contains the sensing pin 292 and a biasing element 293. The sensing pin 292 may extend longitudinally through the housing 291 so that each end 2921, 2922 of the pin emerges from an end the housing 291. The biasing element 293 may comprise a conical compression spring or like biasing element having a first end $293_1$ seated on a first annular support member $291_1$ affixed to the interior surface of the housing 291 adjacent to and spaced from the top 291t of the housing 291 and a second end $293_2$ seated on a second annular support member 2912 affixed to the outer surface of the sensing pin 292 adjacent to and spaced from the second end $292_2$ of the pin 292. The biasing element 293 biases the sensing pin 292 in the direction of the body B so that it extends out through the openings 122 in the bottom wall 114 of the device casing and pad 118 when the pin 292 is not depressed.

Referring still to FIGS. 4A-4D, the mechanical switch assembly 262 may comprise a switch base 266, the depressible UI/actuator 264, and a trigger wire or cable 294 extending through the switch assembly 262. The switch base 266 may comprise a cylindrical side wall 266sw and a bottom wall 266bw closing a bottom end of the side wall 266sw. The central portion of the bottom wall 266bw may be configured to form a receptacle 266r that receives the first end 2921 of the sensing pin 292. The central portion of bottom wall forming the receptacle 266r and the side wall 266sw of the switch base 266 define an annular crimping channel 266c. The UI/actuator 264 may have a cap-like structure comprising a button member 264b and a side wall 264sw depending from perimeter of the button member 264b. The UI/actuator 264 may be telescopically movable relative to the switch base 266 between first and second positions. The button member 264b may include one or more crimp arms 264a that extend from the interior surface thereof and face the crimping channel 266c of the switch base 266. A stop flange 264f may extend outwardly from the bottom edge of the UI/actuator side wall 264sw. The trigger wire 294 may have a first end 2941 anchored to an interior surface, wall, or member 110a of the casing 110 and a second end 2942 operatively connected to trigger the needle insertion drive 150 and/or stopper drive 140 when the trigger wire 294 is crimped between the UI/actuator 264 and the switch base 266, as will be explained further on in greater detail.

Figure 4C:
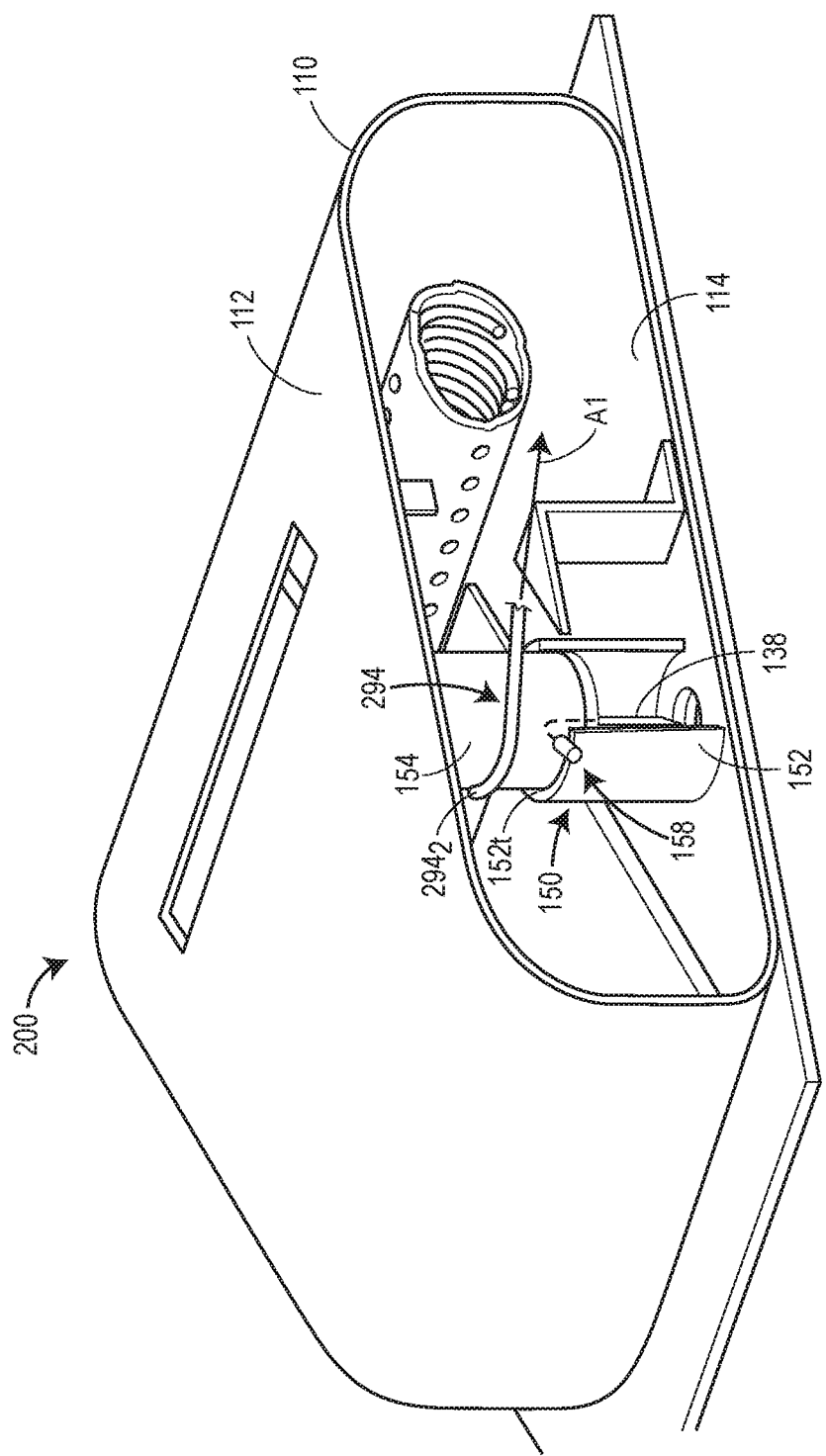
FIG. 4C is cut away perspective view of the device of FIG. 4A which illustrates one non-limiting method for connecting the switch assembly to the needle insertion drive.

FIG. 4C illustrates one non-limiting method for operatively connecting the switch assembly 262 (FIGS. 4A and 4B) to the needle insertion drive 150. As illustrated, the needle insertion drive 150 may comprise a discontinuous or segmented needle holder guide wall 152, a needle holder 154 that holds the injection needle 138, and a compression spring 156 (FIG. 4A) disposed between the needle holder 154 and the top wall 112 of the casing 110 which biases the needle holder 154 towards the needle extended position when the needle holder 154 is raised in the needle concealed position. The needle holder guide wall 152 extends up from the bottom wall 114 of the casing 110 and guides the needle holder 154 as it is propelled down during needle insertion. A lock-out pin 158 or other suitable projection which may extend laterally from the needle holder 154, rests on the top edge 152t of the needle holder guide wall 152 to hold the needle holder 154 in the needle concealed position, prior to activation of the device 200. The second end 2942 or other portion of the trigger wire 294 of the switch assembly 262 may wrap around the needle holder 154. When the UI/actuator 264 (FIGS. 4A and 4B) of the switch assembly 262 is depressed, the trigger wire 294 is pulled in the direction of arrow A1, which in turn rotates the needle holder 154 a few degrees and causes the pin 158 to slide off the top edge 152t of the needle holder guide wall 152, thereby activating the needle insertion drive 150. Once activated, the compressed compression spring 156 of the needle insertion drive 150 propels the needle holder 154 down through the guide wall 152 so that the injection needle 138 extends out from the bottom wall 114 of the casing 110 and penetrates the body tissue of the patient.

Figure 4D:
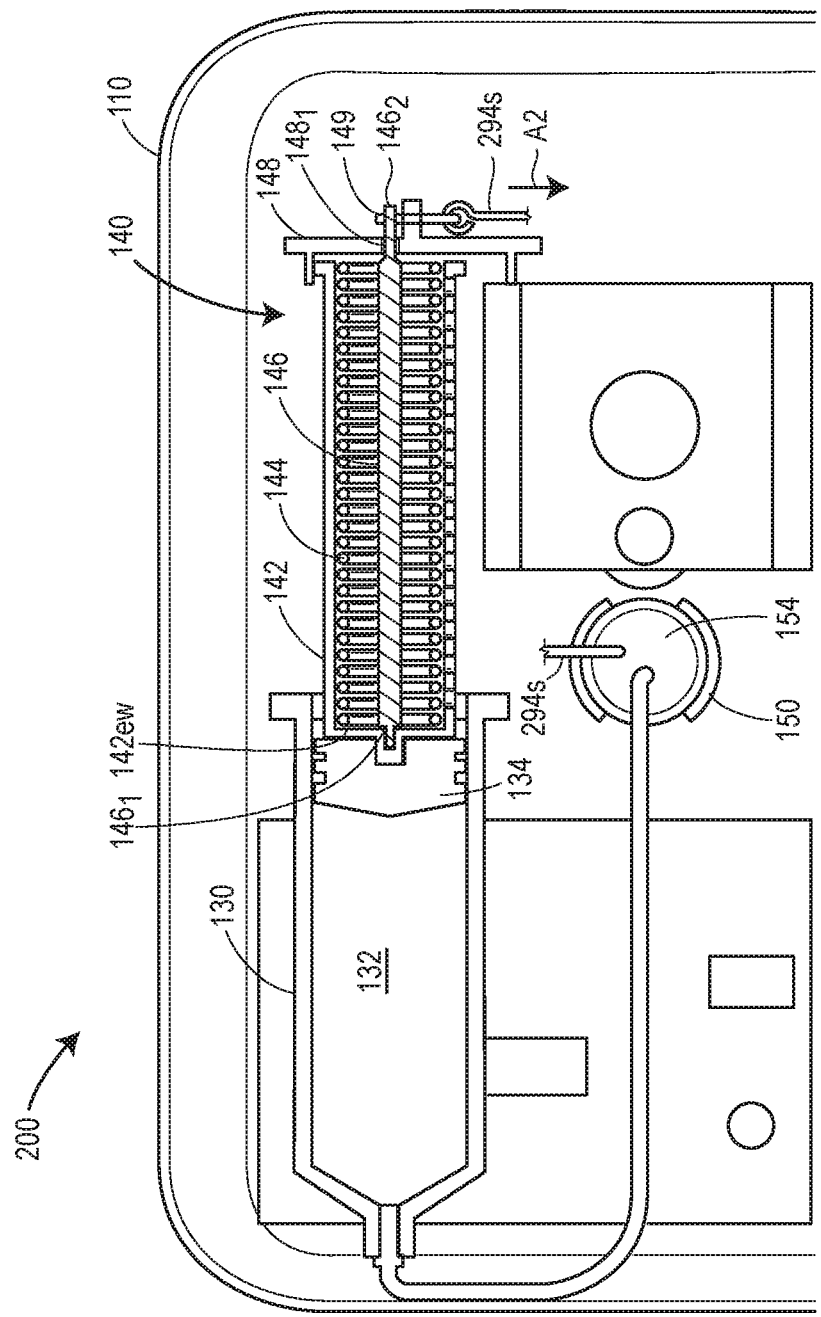
FIG. 4D is a plan view of a portion of the interior of the device of FIG. 4A which illustrates one non-limiting method for connecting the switch assembly to the stopper drive.

FIG. 4D illustrates one non-limiting method for operatively connecting the switch assembly 262 (FIGS. 4A and 4B) to the stopper drive 140. As illustrated, the stopper drive 140 may comprise a hollow plunger 142, a compression spring 144 disposed within the plunger 142 between a working end wall 142ew of the plunger 142 and a backstop wall 148 provided within the casing 110, a spring release rod 146 extending through the spring 144 having a first end 1461 affixed to the working end wall 142ew of the plunger 142 and a second end 1462 extending through an opening 148o in the backstop wall 148, and a delivery lock-out pin 149 which extends through an opening 146o in the second end 1462 of the spring release rod 146. A secondary wire or cable 294s extending from the needle holder 154 of the needle insertion drive 150, may be connected to the lock-out pin 149. Therefore, when the switch assembly 262 activates of the needle insertion drive 150 as described above, the needle holder 154 pulls the secondary wire 294s in the direction of arrow A2, thereby withdrawing the lock-out pin 149 from the opening 146o in the second end 1462 of the spring release rod 146 and thereby releasing it and activating the stopper drive 140. Once activated, the compressed compression spring 144 of the stopper drive 140 propels the plunger 142 against the stopper 134 and drives it through the medicament container 130 to expel the drug 132 stored therein though the injection needle 138 and into the patient's body B.

The UI/actuator 264 may be flush with or recessed from the casing 110 (e.g., top wall 112) when the device 200 is in the not-ready-to-inject state, which is also referred to as the dormant state i.e., where the switch assembly 262 is in the lowered position and the UI/actuator 264 is in the first undepressed position (e.g., the device 200 not properly contacting the body B of the patient). If the patient or operator attempts to depress the UI/actuator 264 to move it from the first position to the second position in the dormant state, the stop flange 264f will engage the top 291t of the body contact sensor housing 291, thereby locking the UI/actuator 264 and preventing the activation of the device 200. Raising switch assembly 262 to the ready state creates a space of gap G between the stop flange 264f and the top 291t of the body contact sensor housing 291 (FIG. 5A), which effectively unlocks the UI/actuator 264 and allows it to be depressed to the second depressed position.

The sensing pin 292 of the body contact sensor 290 raises the switch assembly 262 to the ready state within the casing 110 of the device 200 if the device 200 is properly contacting the body B of the patient such that the body contact sensor 290 occupies the second state to bring the UI/actuator 264 to the attention of the patient or operator and to unlock the UI/actuator 264 and the device activation mechanism 260.

Figure 5C:
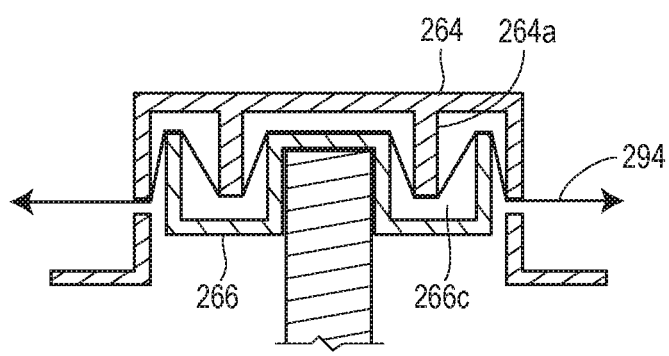
FIG. 5C is an enlarged elevational view of shown the operation of the device activation mechanism illustrated in FIGS. 4A and 4B.
Figure 5A:
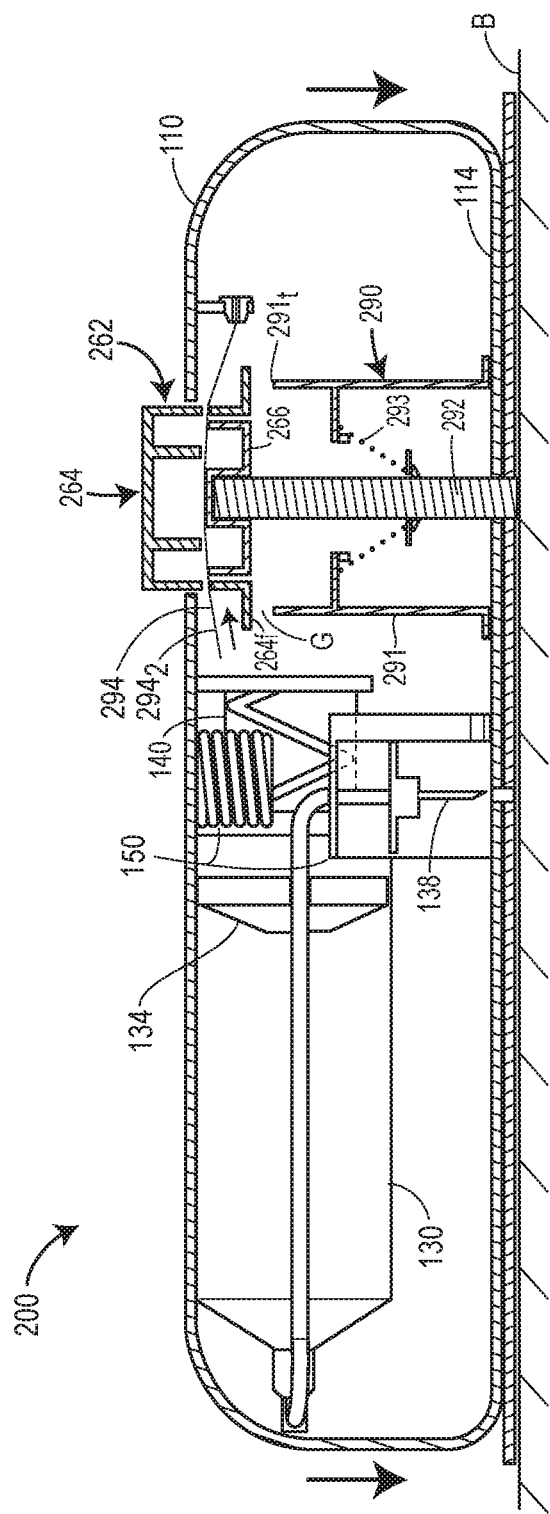
FIGS. 5A and 5B are elevational views with certain elements shown in cross-section, illustrating the operation of the on-body injection device of FIGS. 4A and 4B.
Figure 5B:
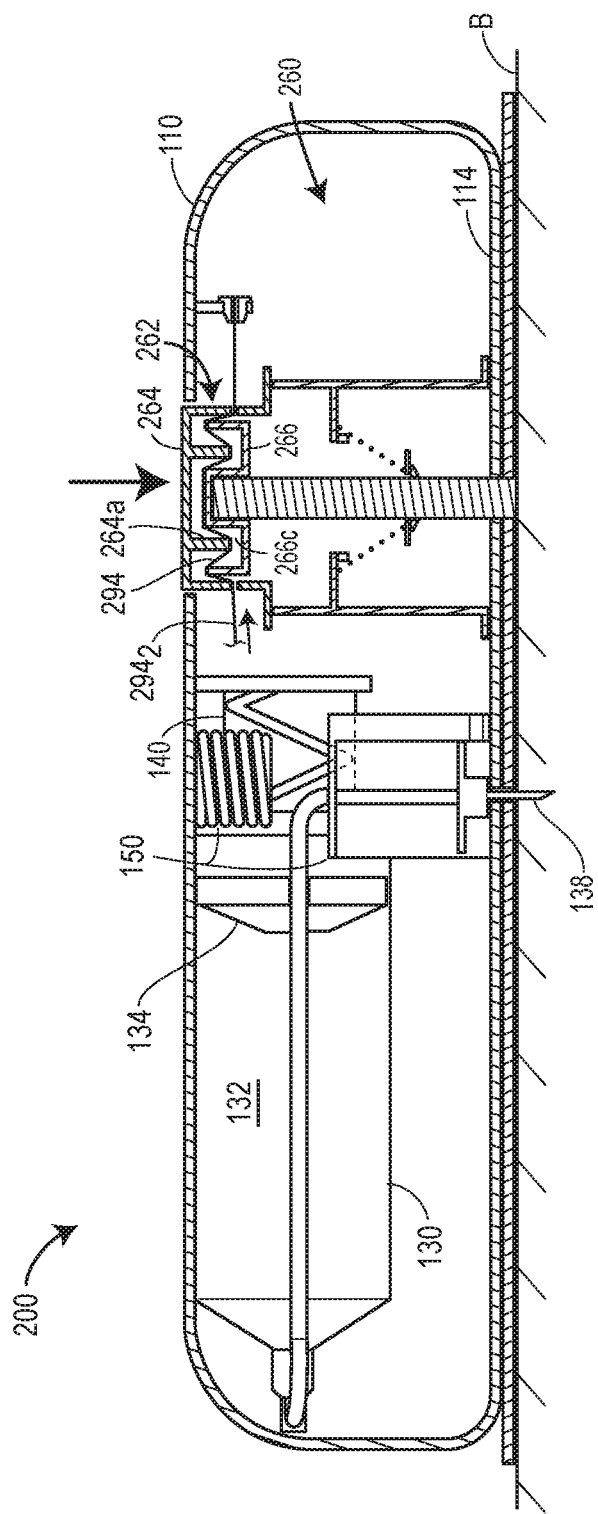

FIGS. 5A-5C illustrate the external state change features of the injection device of FIGS. 4A-4D. FIG. 5A, illustrates the injection device 200 after it has been properly placed in contact with the body B of a patient during the device mounting process. As the device 200 is mounted to the body B, the sensing pin 292 of the body contact sensor 290 retracts into the device casing 110 thereby compressing the biasing element 293 and raising the switch assembly 262 from a lowered position corresponding to the dormant state to and a raised position corresponding to the ready state. The raising of the switch assembly 262 causes the UI/actuator 264 to rise or "pop out" of the device casing 110, thereby drawing the patient's or operator's attention to the UI/actuator 264. The raising of switch assembly 262 also unlocks the UI/actuator 264 (creates the gap G between the stop flange 264f and the top 291t of the body contact sensor housing 291), which places the injection device 200 in the ready-to-inject state, which is also referred to as the ready state. The UI/actuator 264 may now be disposed above the exterior surface of the casing 100 (e.g., top wall 112) as shown in FIG. 5A, or in some other position relative to the casing 110. As the switch assembly 262 rises, the switch base 266 pulls the second end 2942 of the trigger wire 294 which is operatively connected to the needle insertion drive 150 and/or stopper drive 140 toward the switch assembly 262 a first distance, but this distance is not effective for activating the needle insertion drive 150 and/or stopper drive 140.

FIG. 5B illustrates the injection device 200 after the patient or operator has depressed the UI/actuator 264 and moved it from the first undepressed position to the second depressed position, in response to the motion or change in state of the UI/actuator 264 which signals the patient or operator that the next step in the injection administering process is to depress UI/actuator 264. As the UI/actuator 264 is depressed into the second position the crimp arms 264a engage the trigger wire 294 and press it into the crimp channel 266c of the switch base 266, as best shown in FIG. 5C.

Referring again to FIG. 5B, the crimping of the trigger wire 294 pulls the operatively connected second end 2942 of the trigger wire 294 an additional second distance toward the switch assembly 262, which is substantially greater than the first distance. The pulling of the second end 2942 of the trigger wire 294 the first and second distances activates the needle insertion drive 150 to drive the injection needle 138 into the body B of the patient and activates the stopper drive 140, which expels the drug 132 stored in the medicament container 130 though the injection needle 138 and into the patient's body B.

To aid in attracting the attention of the patient or operator, the injection devices described above include state changes represented by physical movements that change the outward appearance of the device activation mechanism 260 by changing the physical location, orientation, and/or configuration of the switch assembly 262 relative to the remainder of the drug delivery device 200. The external state changes, however, may also be configured to illuminate the UI/actuator as it rises, the side wall of the UI/actuator may illuminate or be brightly colored, a sound may be made by an audio speaker contained in the injection device as the UI/actuator rises, a vibration mechanism may be vibrated, and any combination thereof. As such, the outward appearance of the device activation mechanism 260 may be changed by way of lighting and/or exposing a distinctly colored portion that was previously concealed when the device activation mechanism 260 occupied the dormant state. Moreover, while emitting a sound and vibrating the device activation mechanism 260 do not change the outward appearance of the device activation mechanism 260, these do effect an external state change that is recognizable to a user. As such, sounds and vibrations and the like are included within the meaning of external state change used herein.

Figure 6:
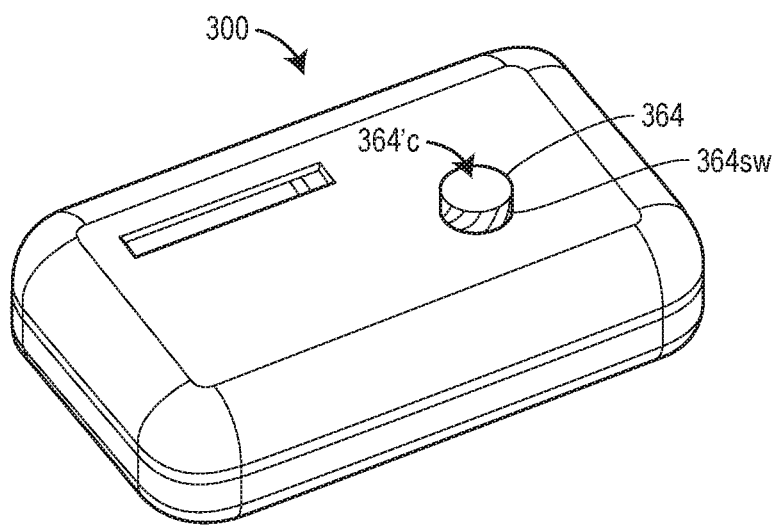
FIG. 6 is perspective view showing the top of an on-body drug injection device according to another embodiment of the disclosure.

FIG. 6 illustrates an embodiment of an on-body injection device 300 which may comprise a button-type UI/actuator 364 which is configured to rotate or spin as they rise or "pop-up" from the dormant state to the ready state, to further attract the attention of the patient or operator. In such embodiments, the UI/actuator 364 may include an icon that spins as the UI/actuator 364 spins, the UI/actuator 364 may illuminate as it spins, the side wall 364sw of the UI/actuator 364 may illuminate or be brightly colored, a sound may be made by an audio speaker (not shown) contained in the injection device 300 as the UI/actuator 364 spins, vibrations may be imparted on the device 300 with a vibration generator, and any combination thereof. Thus, it should be appreciated that the external state change can include physical movement, but can also include non-physical changes such as illumination, audio, tactile (e.g., vibrations), etc. Indeed, in some versions, the state change may not include any physical movement at all, but rather merely simply some audio and/or visual indication.

Figure 7A:
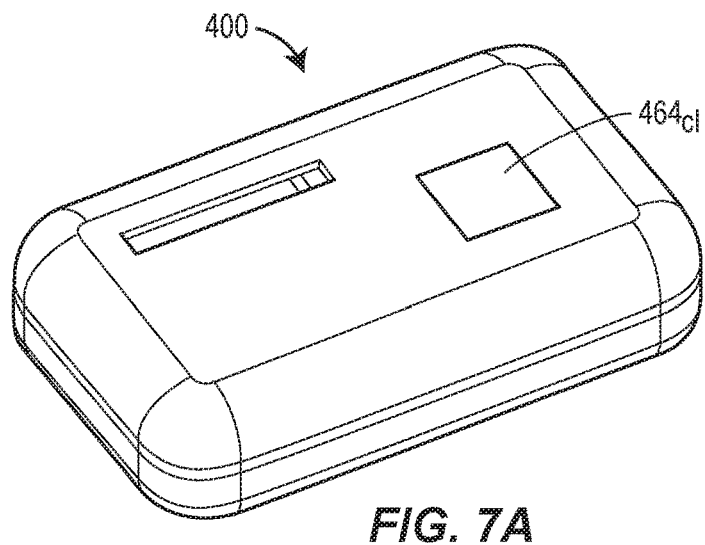
FIGS. 7A-7C are perspective views showing the top of an on-body drug injection device according to a further embodiment of the disclosure.
Figure 7B:
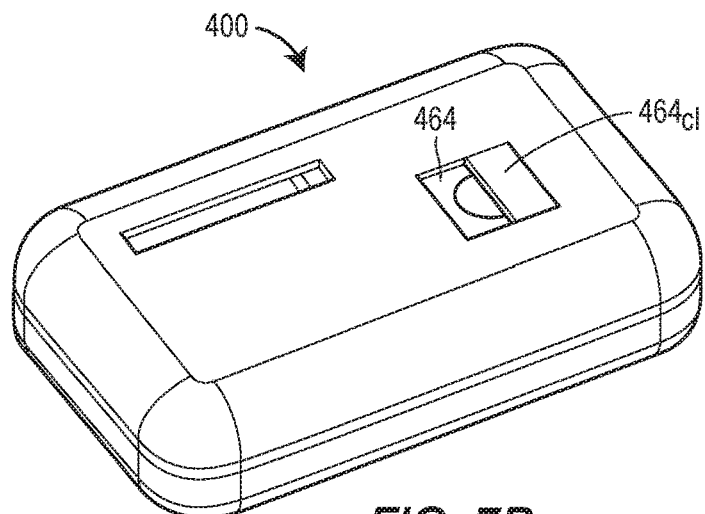
Figure 7C:
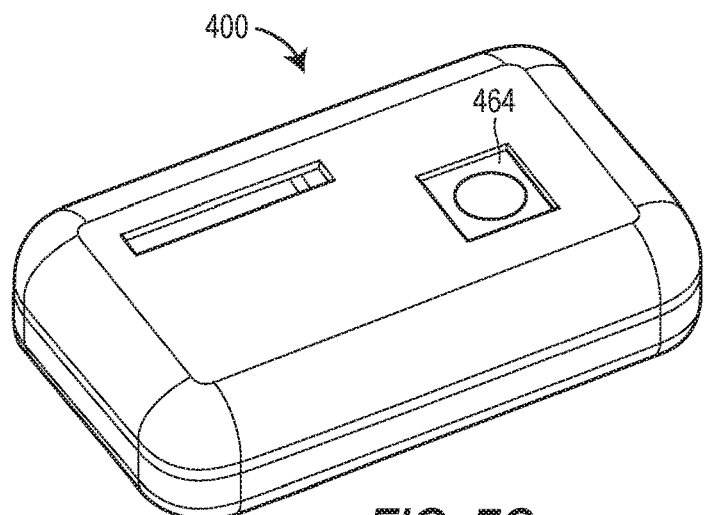

The UI/actuator may also comprise a display that turns on if the body contact sensor of the injection device senses proper contact with the body of the patient, and thereby changes from the dormant state to the ready state, to attract the attention of the patient or operator and signal the next step of the injection process. Such a display would effect change to the outward appearance of the device activation mechanism. FIGS. 7A-7C illustrate an on-body injection device 400 comprising a UI/actuator 464 implemented as a display, such as a capacitive or resistive touchscreen display. The UI/actuator 464 may be concealed behind a closure 464c1 that slidably opens to reveal the UI/actuator display 464, as the body contact sensor (not visible) of the injection device 400 senses proper contact with the body of the patient. In such embodiments, further attention may brought to the UI/actuator display 464 by causing it to display flashing or brightly colored images as it turns on or is revealed by the closure 464c1. In addition, a sound may be combined with the turning on or revealing of the UI/actuator 464 in such embodiments, which sound can be made by an audio speaker (not shown) contained in the injection device 400. Thus, in FIGS. 7A-7C, the external state change can include a dormant state wherein a display is turned off and/or concealed behind the closure 464c1 and the ready state can include the closure 464c1 being removed and/or the display is illuminated or otherwise activated and/or an audio and/or visual signal is emitted.

Figure 8:
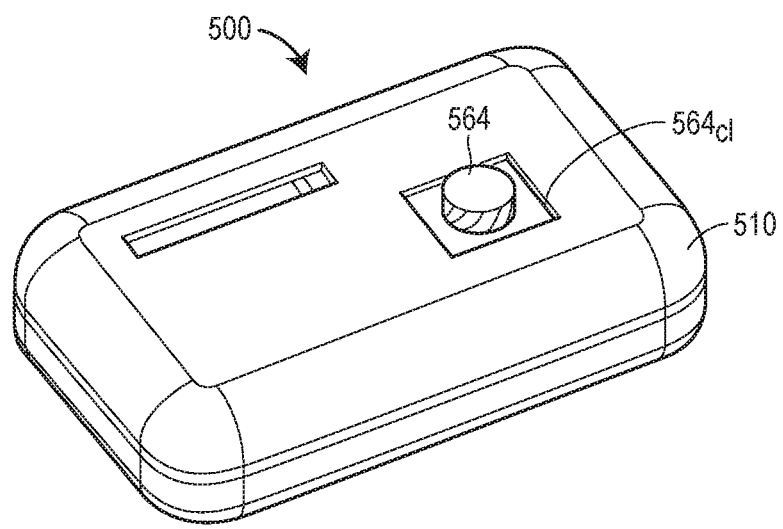
FIG. 8 is a perspective view showing the top of an on-body drug injection device according to a further embodiment of the disclosure.

FIG. 8 illustrates an on-body injection device 500 comprising a button-type UI/actuator 564 concealed by a sliding closure 564c1, which opens as the body contact sensor (not visible) of the injection device 500 senses proper contact with the body of the patient, to allow the UI/actuator 564 to rise or "pop out" from the casing 510.

Figure 9A:
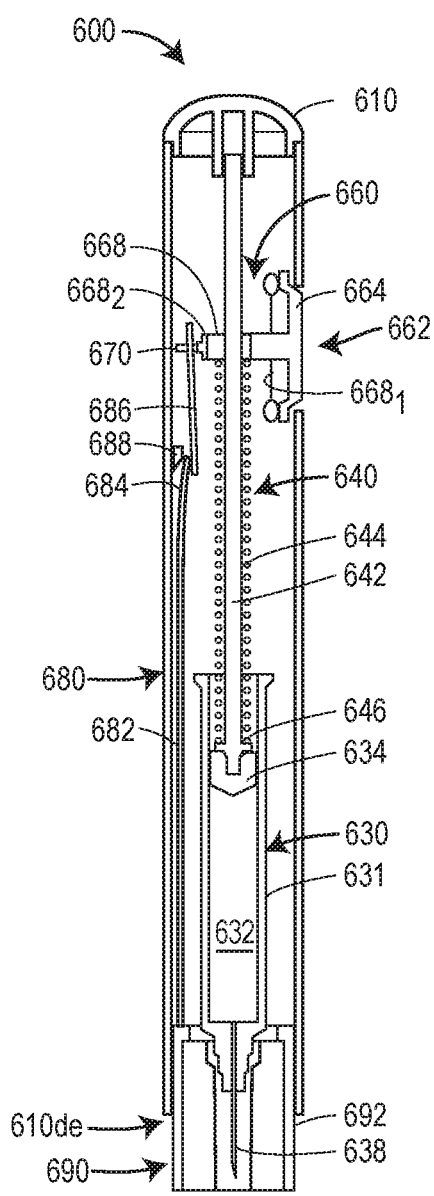
FIG. 9A is an elevational view with certain elements shown in cross-section of a hand-held injection device according to an embodiment of the disclosure.

FIG. 9A illustrates an embodiment of a hand-held injection device 600 according to the present disclosure. The injection device 600 can includes an elongated outer casing 610, a syringe 630 or other medicament container, a stopper drive 640, a device activation mechanism 660, and a body contact sensor 690, and a lift linkage 680.

The syringe 630 can include a barrel 631 for storing a drug 632, an injection needle 638 or any other fluid dispensing element suitable for injecting the drug into the body, and a stopper 634 disposed in the barrel 631 of the syringe 630. In some embodiments, the syringe 630 may be prefilled with the drug 632.

The stopper drive 640 can include a plunger 642 for driving the stopper 634 through the barrel 631 of the syringe 630 to inject the drug 632, and a spring 644 or other energy source for propelling the plunger 642 to perform the drug injection or both needle insertion (e.g., embodiments where the syringe 630 is adapted to axially move relative to the casing) and drug injection. The plunger 642 may extend through the spring 644 so that the one end of the spring 644 engages a head member 646 of the plunger 642 and the other end of the spring 644 engages the device activation mechanism 660. Prior to operation of the injection device 600, the spring 644 may be compressed between the head member 646 of the plunger 642 and the drive activation mechanism 660, thereby generating a spring biasing force against the head member 646 of the plunger 642 and the drive activation mechanism 660. When the injection device 600 is operated by activating the device activation mechanism 660 the spring 644 expands distally thereby propelling the plunger 642.

The device activation mechanism 660 may comprise a mechanical trigger assembly 662 having an actuator 664 that forms the UI, and a plunger release member 668. The UI/actuator 664 may have a button-like structure which is flush with or recessed from the device casing 610 when the device activation mechanism 660 is in the not-ready-to-use state, which is also referred to as a dormant state, i.e., when the trigger assembly 662 is in a first position and the UI/actuator 664 is in an undepressed position. The UI/actuator 664 may be connected to or otherwise disposed at a first end 6681 of a plunger release member 668. A second end 668₂ of the plunger release member 668 may include a sleeve element 670 that slidably receives the lift linkage 680. The plunger release member 668 can include a latch (not visible), which holds the plunger 642 in an armed position prior to operation of the injection device 600 and which releases the plunger 642 when the UP actuator 664 is depressed toward the device casing 610 to activate the injection device 600 to administer an injection. Once released, the spring 644 propels the plunger 642 through the barrel 631 of the syringe 630 thereby driving the stopper 634 and expelling the drug 632 from the barrel 631 and out through the injection needle 638.

The body contact sensor 690 may be a mechanical sensor comprising a tubular sensing member 692 which is also operative as a needle guard. The sensing member 692 can be movably disposed at the distal end 610de of the casing 610, and may be biased in an extended position (corresponding to a first state) by a biasing element (not shown), such as but not limited to a spring, which allows it to retract toward the casing 610 into a second state when the injection device 600 is pressed against the body of the patient. When the sensing member 692 is in the extended position (first state) it may surround or cover the injection needle 638.

The lift linkage 680 connects the sensing member 692 of the body sensor 690 to the trigger assembly 662 of the device activation mechanism 660. The lift linkage 680 may comprise an elongated rod section 682, a bent rod section 684, and a slide rod section 686. The elongated rod section 682 may have one end connected to the sensing member 692 and the other end connected to or merging with an end of the bent rod section 684. The other end of the bent rod section 684 may be connected to merges with an end of the sliding rod section 686. The bent rod section 684 spaces the sliding rod section 686 away from a cam element 688 disposed on the interior surface of the casing 610. The sliding rod section 686 is slidably received within the sleeve element 670 at the second end 6682 of the plunger release member 668.

Figure 9B:
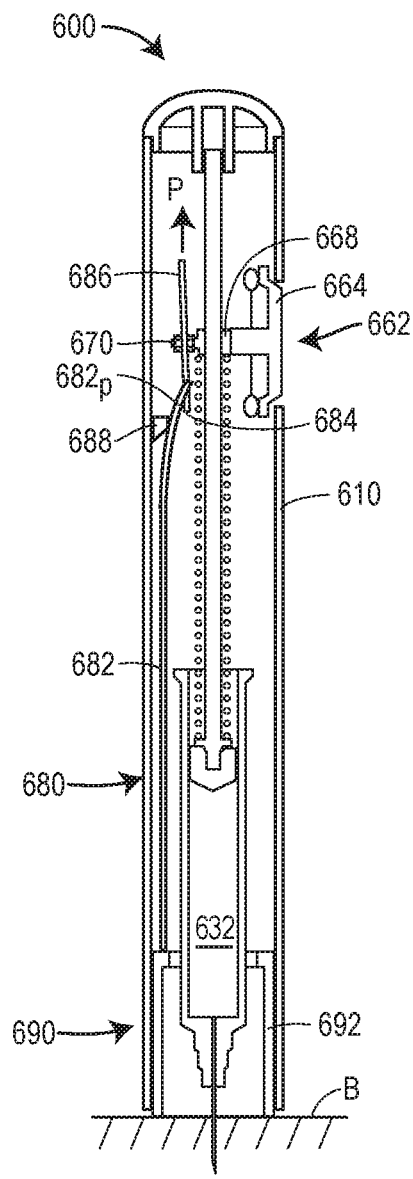
FIG. 9B is an elevational view with certain elements shown in cross-section, illustrating the operation of the hand-held injection device of FIG. 9A.

Referring to FIG. 9B, as the injection device 600 is pressed against the body B of the patient during the process of administering an injection, the sensing member 692 of the body contact sensor 690 retracts proximally into the casing 610 to occupy the second state, thereby moving the lift linkage 680 proximally (arrow P). As the lift linkage 680 moves proximally, the sliding rod section 686 can slide freely through the sleeve element 670 of the plunger release member 668, while remaining connected therewith. The length of the bent rod section 684 is selected so that when a body contact threshold is reached, a proximal end 682p of the elongated rod section engages the cam 688 disposed on the interior surface of the device casing 610 and deflects the elongated rod section 682 toward the plunger release member 668. The deflection of the elongated rod section 682 causes the sliding rod section 686 to move the trigger assembly 662 laterally within the device casing 610 thereby causing the UI/actuator 664 to rise or "pop out" from its dormant state in the casing 610 to a ready state out of the casing. The rising, "pop out," or other external state change draws attention to the UI/actuator 664 and signals the next step in the injection administering process.

In some embodiments of hand-held injection device, the button-type UI/actuator may also be configured to rotate or spin as it undergoes change from the dormant state to the ready state to further attract the attention of the patient or operator. In such embodiments, the UI/actuator may include an icon that spins as the UI/actuator spins, or moreover, the UI/actuator may illuminate as it spins, the side wall of the UI/actuator may illuminate or be brightly colored, a sound may be made by an audio speaker contained in the injection device as the UI/actuator spins, and any combination thereof. In other embodiment of the hand-held injection device, the button-type UI/actuator and the attention enhancements described above may also be concealed by a closure which opens to allow the UI/actuator to rise or "pop out."

In still further embodiments, the UI/actuator of the hand-held injection device may also comprise a display that turns on if the body contact sensor of the injection device senses proper contact with the body of the patient to attract the attention of the patient or operator and signal the next step of the injection process. In some embodiments, the display may also be concealed by a closure that opens to reveal the UI/actuator display, as the body contact sensor of the injection device senses proper contact with the body of the patient. In such embodiments, further attention may brought to the UI/actuator-display by causing it to display flashing or brightly colored images as it turns on or is revealed by the closure. In addition, a sound may be combined with the turning on or revealing of the UI/actuator in such embodiments, which sound can be made by an audio speaker contained in the injection device.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (?4), deposited at the ATCC under number PTA-5214, and a light chain encoded by a polynucleotide in plasmid 15H12/19D12 LCF (?), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4137 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-?4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100);

anti-LLY antibody; BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery device, systems, and methods have been described in terms of illustrative embodiments, it is not limited thereto. Rather, the appended claims should be construed broadly to include other variants and embodiments of same, which may be made by those skilled in the art without departing from the scope and range of equivalents of the device, system, and method.

What is claimed is:
1. An on-body drug delivery device comprising:
a casing having a top wall, a bottom wall, and side walls extending between the top wall and the bottom wall, the bottom wall having an opening extending therethrough;
a container for storing a drug received within the casing, the container having a longitudinal axis;
a stopper movably disposed within the container for expelling the drug;
a drug delivery member fluidly coupled to the container, the drug delivery member extending along an injection axis transverse to the longitudinal axis of the container and being selectively movable to an injection position extending outwardly from the casing through the opening in the bottom wall along the injection axis;
an injection drive comprising an energy source operably coupled to the stopper for selectively moving the stopper through the container to expel the drug;
a sensor having a first state when the drug delivery device is out of contact with a body of a patient, and having a second state when the drug delivery device is in contact with the body of the patient;
a device activation mechanism operably coupled to the sensor and the injection drive for selectively activating the injection drive, wherein the device activation mechanism undergoes an external state change from a dormant state, when the sensor occupies the first state, to a ready state indicating that the on-body drug delivery device is ready for at least one of injection or insertion and awaiting further input to proceed with the at least one of injection or insertion, in response to the sensor changing from the first state to the second state; and
an adhesive pad completely covering an outer surface of the bottom wall of the casing to removably attach the casing to the body of the patient, the adhesive pad defining an opening aligned with the opening extending through the bottom wall to receive the drug delivery member therethrough,
wherein the device activation mechanism is moveable relative to an outer surface of the casing between a lowered position, wherein the entire device activation mechanism is below the outer surface of the casing when in the dormant state, and a raised position when in the ready state.
2. The on-body drug delivery device according to claim 1, wherein in the lowered position, an outer surface of the device activation mechanism is below the outer surface of the casing and in the raised position, the outer surface of the device activation mechanism is between the lowered position and the outer surface of the casing.

3. The on-body drug delivery device according to claim 1, wherein in the raised position, an outer surface of the device activation mechanism is above the outer surface of the casing.

4. The on-body drug delivery device according to claim 1, wherein the device activation mechanism includes a surface that is exposed when in the ready state and wherein the surface includes a changed color from a previous color, a distinct color relative to a remainder of the device, an illuminated surface, or a combination thereof.

5. The on-body drug delivery device according to claim 1, wherein at least a portion of the device activation mechanism rotates as it moves between the dormant and ready states.

6. The on-body drug delivery device according to claim 1, wherein the device activation mechanism is at least one of mechanically coupled to the sensor, electrically coupled to the sensor, and electromechanically coupled to the sensor.

7. The on-body drug delivery device according to claim 1, comprising a first linkage mechanically coupling the device activation mechanism to the sensor.

8. The on-body drug delivery device according to claim 1, wherein the device activation mechanism is provided in association with at least one indicator that activates when the device activation mechanism occupies the ready state, the indicator comprising at least one of a light source, an audio source, a vibration source, or a graphical display.

9. The on-body drug delivery device of claim 1, wherein the sensor comprises at least one of: a mechanical sensor, an electromechanical sensor, a capacitive sensor, a resistive sensor, an impedance sensor, a proximity sensor, an infrared sensor, and a distance sensor.

10. The on-body drug delivery device according to claim 9, wherein the sensor comprises a mechanical sensing member movable between a first position when the sensor occupies the first state and a second position when the sensor occupies the second state.

11. The on-body drug delivery device of claim 1, wherein the energy source comprises at least one of: one or more springs, a gas pressure or gas releasing arrangement, or one or more motors.

12. The on-body drug delivery device of claim 1, wherein the drug delivery member comprises an injection needle coupled to the container.

13. The on-body drug delivery device of claim 1, further comprising a processor, and wherein the sensor is adapted to send a signal to the processor in response to changing from the first state to the second state; and the processor is configured to control operation of an activation sequence of the injection drive in response to receiving the signal.

14. The on-body drug delivery device of claim 13, wherein the sensor is adapted to send a second signal to the processor in response to changing from the second state to the first state; and the processor is configured to control operation of a deactivation sequence of the injection drive in response to receiving the second signal.

15. The on-body drug delivery device of claim 1, wherein the sensor comprises a deflectable sensing pin extending through the casing, deflection of the sensing pin causing the sensor to change from the first state to the second state.

16. The on-body drug delivery device of claim 1, wherein the casing comprises a closure or removable portion allowing removal of the container from the casing and insertion of the container into the casing.

* * * * *